United States Patent
Powell et al.

(10) Patent No.: US 11,628,176 B2
(45) Date of Patent: Apr. 18, 2023

(54) COMBINATIONAL DRUG THERAPIES

(71) Applicant: Opna Bio SA, Epalinges (CH)

(72) Inventors: Ben Powell, Pleasant Hill, CA (US); Athanasios Tsiatis, San Francisco, CA (US); Jackie Walling, Hillsborough, CA (US)

(73) Assignee: OPNA BIO SA, Epalinges (CH)

( * ) Notice: Subject to any disclaimer, the term of this patent is extended or adjusted under 35 U.S.C. 154(b) by 0 days.

(21) Appl. No.: 17/407,811

(22) Filed: Aug. 20, 2021

(65) Prior Publication Data
US 2022/0054507 A1    Feb. 24, 2022

Related U.S. Application Data

(60) Provisional application No. 63/069,637, filed on Aug. 24, 2020, provisional application No. 63/068,973, filed on Aug. 21, 2020.

(51) Int. Cl.
| | |
|---|---|
| *A61K 31/58* | (2006.01) |
| *A61P 35/00* | (2006.01) |
| *A61K 31/4166* | (2006.01) |
| *A61K 31/444* | (2006.01) |
| *A61K 31/502* | (2006.01) |
| *A61K 31/573* | (2006.01) |

(52) U.S. Cl.
CPC .......... *A61K 31/58* (2013.01); *A61K 31/4166* (2013.01); *A61K 31/444* (2013.01); *A61K 31/502* (2013.01); *A61K 31/573* (2013.01); *A61P 35/00* (2018.01)

(58) Field of Classification Search
None
See application file for complete search history.

(56) References Cited

U.S. PATENT DOCUMENTS

| | | |
|---|---|---|
| 7,202,266 B2 | 4/2007 | Arnold et al. |
| 7,348,338 B2 | 3/2008 | Arnold et al. |
| 7,476,746 B2 | 1/2009 | Artis et al. |
| 7,491,831 B2 | 2/2009 | Artis et al. |
| 7,504,509 B2 | 3/2009 | Ibrahim et al. |
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,759,475 B2 | 7/2010 | West |
| 7,846,941 B2 | 12/2010 | Zhang et al. |
| 7,863,288 B2 | 1/2011 | Ibrahim et al. |
| 7,893,075 B2 | 2/2011 | Zhang et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Ibrahim et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,470,821 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Ibrahim et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |

(Continued)

OTHER PUBLICATIONS

U.S. Appl. No. 17/180,212, filed Feb. 19, 2021, Ibrahim et al.
U.S. Appl. No. 17/478,148, filed Sep. 17, 2021, Desai et al.
U.S. Appl. No. 14/501,850, filed Oct. 14, 2021, Ibrahim et al.
U.S. Appl. No. 17/477,240, filed Sep. 16, 2021, Zhang et al.
U.S. Appl. No. 17/335,898, filed Jun. 1, 2021, Wu et al.
U.S. Appl. No. 17/372,330, filed Jul. 9, 2021, Wu et al.
U.S. Appl. No. 17/372,346, filed Jul. 9, 2021, Wu et al.

(Continued)

*Primary Examiner* — Nannette Holloman
(74) *Attorney, Agent, or Firm* — Elmore Patent Law Group, P.C.; Joseph C. Zucchero

(57) ABSTRACT

Disclosed is a method of treating a subject suffering from a cancer, comprising administering to the subject a combination of agents comprising:
(a) Compound I:

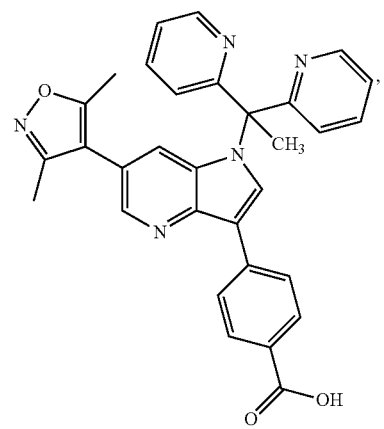

or a pharmaceutically acceptable salt thereof; and
(b) one or more inhibitors of the androgen receptor signaling pathway; or
(c) one or more PARP inhibitors;
wherein the amount of the combination of agents is therapeutically effective in the treatment.

25 Claims, 11 Drawing Sheets

(56) References Cited

U.S. PATENT DOCUMENTS

| | | |
|---|---|---|
| 9,096,593 B2 | 8/2015 | Zhang et al. |
| 9,150,570 B2 | 10/2015 | Ibrahim |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,682,981 B2 | 6/2017 | Zhang et al. |
| 9,695,169 B2 | 7/2017 | Ibrahim et al. |
| 9,718,847 B2 | 8/2017 | Zhang et al. |
| 9,730,918 B2 | 8/2017 | Bollag et al. |
| 9,745,298 B2 | 8/2017 | Ibrahim et al. |
| 9,771,363 B2 | 9/2017 | Ibrahim et al. |
| 9,771,369 B2 | 9/2017 | Lin et al. |
| 9,776,998 B2 | 10/2017 | Ibrahim et al. |
| 9,802,932 B2 | 10/2017 | Ibrahim et al. |
| 9,814,714 B2 | 11/2017 | Ibrahim et al. |
| 9,822,109 B2 | 11/2017 | Zhang et al. |
| 9,844,539 B2 | 12/2017 | Wu et al. |
| 9,856,259 B2 | 1/2018 | Shi et al. |
| 9,873,700 B2 | 1/2018 | Zhang et al. |
| 9,938,273 B2 | 4/2018 | Wu et al. |
| 9,975,894 B2 | 5/2018 | Ibrahim et al. |
| 9,994,567 B2 | 6/2018 | Ibrahim et al. |
| 10,040,792 B2 | 8/2018 | Ibrahim et al. |
| 10,123,998 B2 | 11/2018 | Bollag et al. |
| 10,160,747 B2 | 12/2018 | Lin et al. |
| 10,160,755 B2 | 12/2018 | Lin et al. |
| 10,189,833 B2 | 1/2019 | Ibrahim et al. |
| 10,227,357 B2 | 3/2019 | Lin et al. |
| 10,316,032 B2 | 6/2019 | Ibrahim et al. |
| 10,370,374 B2 | 8/2019 | Ibrahim et al. |
| 10,399,975 B2 | 9/2019 | Ibrahim et al. |
| 10,421,761 B2 | 9/2019 | Zhang et al. |
| 10,426,760 B2 | 10/2019 | Wu et al. |
| 10,428,067 B2 | 10/2019 | Zhang et al. |
| 10,435,404 B2 | 10/2019 | Ibrahim et al. |
| 10,501,460 B2 | 12/2019 | Zhang et al. |
| 10,508,085 B2 | 12/2019 | Zhang et al. |
| 10,519,177 B2 | 12/2019 | Zhang et al. |
| 10,577,366 B2 | 3/2020 | Lin et al. |
| 10,584,122 B2 | 3/2020 | Ibrahim et al. |
| 10,647,716 B2 | 5/2020 | Ibrahim et al. |
| 10,703,757 B2 | 7/2020 | Wu et al. |
| 10,717,735 B2 | 7/2020 | Ibrahim et al. |
| 10,730,876 B2 | 8/2020 | Ibrahim et al. |
| 10,829,484 B2 | 11/2020 | Holladay et al. |
| 10,899,761 B2 | 1/2021 | Ibrahim et al. |
| 10,941,142 B2 | 3/2021 | Ibrahim et al. |
| 10,961,240 B2 | 3/2021 | Ibrahim et al. |
| 2017/0157120 A1 | 6/2017 | Ibrahim et al. |
| 2018/0265508 A1* | 9/2018 | Lin ................... A61K 31/437 |
| 2019/0125747 A1 | 5/2019 | Rezaei et al. |
| 2019/0300487 A1 | 10/2019 | Zhang et al. |
| 2020/0299293 A1 | 9/2020 | Ibrahim et al. |
| 2021/0198239 A1 | 7/2021 | Vander et al. |
| 2021/0315869 A1 | 10/2021 | Albers et al. |
| 2021/0315872 A1 | 10/2021 | Spevak et al. |

OTHER PUBLICATIONS

U.S. Appl. No. 17/238,076, filed Apr. 22, 2021, Ibrahim et al.
U.S. Appl. No. 17/387,775, filed Jul. 28, 2021, Ibrahim et al.
U.S. Appl. No. 17/368,582, filed Jul. 6, 2021, Ibrahim et al.
U.S. Appl. No. 17/379,837, filed Jul. 9, 2021, Rezaei et al.
U.S. Appl. No. 17/238,121, filed Apr. 22, 2021, Shi et al.
U.S. Appl. No. 17/480,111, filed Sep. 20, 2021, Zhang et al.
Adashek, J. J. et al., "Clinical Development of PARP Inhibitors in Treating Metastatic Castration-Resistant Prostate Cancer", Cells, 8(8), https://doi.org/10.3390/cells8080860, 2019, 860.
Schweizer, M. T. et al., "Abiraterone and other novel androgen-directed strategies for the treatment of prostate cancer: a new era of hormonal therapies is born", Ther. Adv. in Urology, 4(4), DOI: 10.1177/1756287212452196, Aug. 1, 2012, 167-178.

* cited by examiner

Figure 2A

N=3, Compound I [μM]

| enzalutamide [μM] | 0 | 0.004 | 0.012 | 0.037 | 0.11 | 0.33 | 1 |
|---|---|---|---|---|---|---|---|
| 0 | 100 ±0 | 110 ±4 | 56 ±0 | 34 ±1 | 26 ±2 | 24 ±1 | 19 ±0 |
| 0.12 | 103 ±4 | 75 ±3 | 41 ±2 | 26 ±2 | 20 ±1 | 16 ±1 | 14 ±0 |
| 0.37 | 74 ±3 | 61 ±3 | 36 ±1 | 25 ±1 | 20 ±1 | 16 ±1 | 14 ±0 |
| 1 | 64 ±5 | 55 ±1 | 35 ±2 | 25 ±1 | 19 ±1 | 15 ±1 | 13 ±0 |
| 3 | 55 ±2 | 49 ±3 | 33 ±1 | 24 ±1 | 19 ±1 | 15 ±1 | 13 ±1 |
| 10 | 60 ±2 | 44 ±3 | 29 ±2 | 23 ±1 | 18 ±0 | 15 ±1 | 13 ±0 |
| 30 | 47 ±3 | 35 ±1 | 26 ±1 | 20 ±1 | 16 ±1 | 14 ±0 | 12 ±0 |

% Control

Figure 2B

N=3, Compound I [μM]

| enzalutamide [μM] | 0.004 | 0.012 | 0.037 | 0.11 | 0.33 | 1 |
|---|---|---|---|---|---|---|
| 0.12 | -1 ±3 | 15 ±2 * | 7 ±2 * | 3 ±1 * | 4 ±1 * | 6 ±0 * |
| 0.37 | -1 ±3 | 20 ±1 * | 7 ±1 * | 3 ±1 | 4 ±1 * | 6 ±0 ** |
| 1.1 | 1 ±1 | 21 ±2 * | 7 ±1 * | 4 ±1 * | 5 ±1 * | 6 ±0 *** |
| 3 | 6 ±3 | 22 ±1 ** | 9 ±1 * | 4 ±1 * | 5 ±1 * | 6 ±1 * |
| 10 | 11 ±3 * | 26 ±2 * | 10 ±1 * | 5 ±0 ** | 6 ±1 * | 7 ±0 * |
| 30 | 21 ±1 ** | 30 ±1 ** | 12 ±1 * | 7 ±1 * | 7 ±0 * | 8 ±0 ** |

Loewe Score

Figure 3A

N=3, Compound I [µM]

| enzalutamide [µM] | 0 | 0.004 | 0.012 | 0.037 | 0.11 | 0.33 | 1 |
|---|---|---|---|---|---|---|---|
| 0.00 | 100 ±0 | 87 ±6 | 62 ±1 | 44 ±2 | 30 ±3 | 27 ±1 | 21 ±1 |
| 0.41 | 98 ±3 | 75 ±3 | 54 ±1 | 36 ±2 | 26 ±3 | 20 ±1 | 17 ±1 |
| 1.2 | 91 ±3 | 80 ±3 | 59 ±1 | 39 ±2 | 28 ±2 | 22 ±1 | 18 ±0 |
| 3.7 | 92 ±1 | 81 ±6 | 56 ±2 | 39 ±2 | 26 ±2 | 21 ±1 | 18 ±1 |
| 11 | 82 ±2 | 69 ±1 | 51 ±0 | 33 ±2 | 24 ±1 | 20 ±1 | 17 ±1 |
| 33 | 64 ±4 | 52 ±1 | 39 ±4 | 26 ±2 | 20 ±1 | 17 ±2 | 14 ±1 |
| 100 | 13 ±1 | 13 ±1 | 9 ±0 | 7 ±0 | 7 ±1 | 5 ±0 | 4 ±0 |

% Control

Figure 3B

N=3, Compound I [µM]

| enzalutamide [µM] | 0.004 | 0.012 | 0.037 | 0.11 | 0.33 | 1 |
|---|---|---|---|---|---|---|
| 0.41 | 4 ±3 | 8 ±1 * | 8 ±2 * | 5 ±3 | 5 ±1 * | 5 ±1 * |
| 1.2 | -1 ±3 | 2 ±1 * | 4 ±2 | 3 ±2 | 3 ±1 * | 4 ±0 ** |
| 3.7 | -5 ±6 | 4 ±2 | 4 ±2 | 5 ±2 * | 3 ±1 * | 4 ±1 * |
| 11 | -2 ±1 | 3 ±0 * | 7 ±2 * | 6 ±1 * | 4 ±1 * | 4 ±1 * |
| 33 | -9 ±1 * | -1 ±4 | 6 ±2 * | 6 ±1 * | 5 ±2 * | 8 ±1 * |
| 100 | 2 ±1 | 5 ±0 * | 7 ±0 ** | 8 ±1 * | 10 ±0 ** | 11 ±0 ** |

Loewe Score

Compound I [μM]

| abiraterone acetate [μM] | 0 | 0.004 | 0.012 | 0.037 | 0.11 | 0.33 | 1 |
|---|---|---|---|---|---|---|---|
| 0.00 | 100 ±0 | 102 ±6 | 51 ±1 | 31 ±1 | 25 ±1 | 22 ±1 | 18 ±1 |
| 0.41 | 105 ±13 | 82 ±4 | 43 ±1 | 25 ±1 | 21 ±1 | 17 ±1 | 14 ±1 |
| 1.2 | 58 ±2 | 48 ±4 | 33 ±2 | 24 ±1 | 21 ±1 | 18 ±0 | 15 ±1 |
| 3.7 | 32 ±1 | 30 ±1 | 25 ±1 | 20 ±1 | 17 ±1 | 15 ±1 | 13 ±0 |
| 11 | 22 ±0 | 21 ±1 | 19 ±0 | 16 ±1 | 14 ±1 | 13 ±1 | 11 ±1 |
| 33 | 17 ±2 | 15 ±2 | 12 ±0 | 9 ±1 | 8 ±0 | 7 ±0 | 6 ±0 |
| 100 | 9 ±1 | 8 ±2 | 4 ±1 | 2 ±1 | 2 ±0 | 2 ±0 | 1 ±1 |

% Control

Compound I [μM]

| abiraterone acetate [μM] | 0.004 | 0.012 | 0.037 | 0.11 | 0.33 | 1 |
|---|---|---|---|---|---|---|
| 0.41 | -19 ±4 * | 3 ±1 * | 5 ±1 * | 2 ±1 * | 4 ±1 * | 7 ±1 * |
| 1.2 | 1 ±4 | 7 ±2 * | 4 ±1 * | 2 ±1 | 3 ±0 * | 6 ±1 * |
| 3.7 | 3 ±1 * | 5 ±1 * | 5 ±1 * | 4 ±1 * | 6 ±1 * | 8 ±0 ** |
| 11 | 0 ±1 | 2 ±0 * | 5 ±1 * | 6 ±1 * | 7 ±1 * | 10 ±1 * |
| 33 | -1 ±2 | 2 ±0 * | 5 ±1 * | 6 ±0 ** | 6 ±0 ** | 8 ±0 ** |
| 100 | 2 ±2 | 6 ±1 * | 8 ±1 * | 8 ±0 ** | 8 ±0 * | 9 ±1 * |

Loewe Score

Figure 5A

N=3, Compound I [μM]

| abiraterone acetate [μM] | 0 | 0.004 | 0.012 | 0.037 | 0.11 | 0.33 | 1 |
|---|---|---|---|---|---|---|---|
| 0.00 | 100 ±0 | 87 ±5 | 59 ±2 | 42 ±1 | 28 ±1 | 25 ±1 | 20 ±1 |
| 0.41 | 105 ±6 | 85 ±5 | 59 ±3 | 37 ±0 | 27 ±1 | 23 ±1 | 17 ±1 |
| 1.2 | 104 ±2 | 89 ±4 | 64 ±3 | 42 ±3 | 30 ±1 | 25 ±0 | 21 ±0 |
| 3.7 | 98 ±2 | 79 ±2 | 59 ±3 | 39 ±3 | 29 ±2 | 24 ±2 | 19 ±1 |
| 11 | 57 ±1 | 50 ±1 | 38 ±2 | 28 ±2 | 23 ±0 | 20 ±1 | 18 ±1 |
| 33 | 26 ±1 | 25 ±7 | 20 ±1 | 14 ±1 | 13 ±2 | 11 ±1 | 11 ±1 |
| 100 | 31 ±4 | 30 ±1 | 23 ±2 | 16 ±0 | 11 ±0 | 11 ±1 | 9 ±1 |

% Control

Figure 5B

N=3, Compound I [μM]

| abiraterone acetate [μM] | 0.004 | 0.012 | 0.037 | 0.11 | 0.33 | 1 |
|---|---|---|---|---|---|---|
| 0.41 | -7 ±5 | 1 ±3 | 3 ±0 * | 2 ±1 | 1 ±1 | 4 ±1 * |
| 1.2 | -12 ±4 * | -6 ±3 | -3 ±3 | -2 ±1 * | -1 ±0 * | 0 ±0 |
| 3.7 | -8 ±2 * | -6 ±3 | -2 ±3 | -1 ±2 | -1 ±2 | 2 ±1 |
| 11 | -5 ±1 * | 0 ±2 | 3 ±2 | 3 ±0 * | 3 ±1 * | 3 ±1 * |
| 33 | 1 ±7 | 6 ±1 * | 12 ±1 * | 13 ±2 * | 12 ±1 * | 10 ±1 * |
| 100 | -4 ±1 * | 3 ±2 | 9 ±0 ** | 14 ±0 ** | 12 ±1 * | 12 ±1 * |

Loewe Score

COMBINATIONAL DRUG THERAPIES

CROSS-REFERENCE TO RELATED APPLICATIONS

This application claims the benefit under 35 U.S.C. § 119(e) to U.S. Provisional Application No. 63/068,973, filed Aug. 21, 2020, and U.S. Provisional Application No. 63/069,637, filed Aug. 24, 2020 each of which is incorporated herein by reference in its entirety.

FIELD

The present disclosure relates to novel combinational therapies for treating a subject with a cancer, in particular a solid tumor, for example, prostate cancer, comprising administering to the subject 4-(1-(1,1-di(pyridin-2-yl)ethyl)-6-(3,5-dimethylisoxazol-4-yl)-1H-pyrrolo[3,2-b]pyridin-3-yl)benzoic acid, or a pharmaceutically acceptable salt thereof, and one or more androgen receptor pathway inhibitors.

BACKGROUND

Prostate cancer is the most commonly diagnosed cancer affecting men in the United States. The prostate is a hormone-dependent gland in which androgen hormones testosterone and dihydrotestosterone bind to and activate the androgen receptor, initiating nuclear translocation of androgen receptor and a subsequent signaling cascade. Due to the androgen dependency of the prostate, androgen deprivation therapies have emerged as first line treatment for aggressive prostate cancer. Such therapies are effective until the point at which prostate cancer, through a variety of mechanisms including, but not limited to, generation of ligand-independent androgen receptor splice variants, or intratumoral androgen production, overcome hormone deprivation. These cancers are androgen ablation resistant, clinically termed castration resistant prostate cancer (CRPC) and remain incurable. First-generation antiandrogens established androgen receptor blockade as a therapeutic strategy, but these therapies do not completely block androgen receptor activity. However, resistance to these drugs often occurs after 2-3 years as the patients develop castration-resistant prostate cancer (CRPC). In CRPC, a functional AR remains a key regulator. (Tam et al, *Androgen receptor: structure, role in prostate cancer and drug discovery*, Acct Pharmacologica Sinica volume 36, (2015)).

Efficacy and potency have been improved by the development of second-generation antiandrogen therapies, which remain the standard of care for patients with CRPC. Four second-generation anti-androgens are currently approved by the Food and Drug Administration (FDA); abiraterone acetate, enzalutamide, and recently approved apalutamide and darolutamide. (Rice et al., Second-Generation Antiandrogens: From Discovery to Standard of Care in Castration Resistant Prostate Cancer Front. Oncol., 28 Aug. 2019 https://doi.org/10.3389/fonc.2019.00801).

Abiraterone was the first hormonal agent FDA approved to increase survival. Abiraterone is a potent inhibitor of CYP17 that is a key enzyme in testosterone synthesis, thus and interferes with steroid metabolism resulting in loss of testosterone. Targeting of the androgen-androgen receptor (AR) signaling pathway either by blocking androgen synthesis or blocking androgenic effects has been standard of care for men with advanced prostate cancer. (Schweizer et al., Abiraterone and other novel androgen-directed strategies for the treatment of prostate cancer: a new era of hormonal therapies is born, *Ther Adv Urol.* 2012 August; 4(4): 167-178). It has been demonstrated that androgen-responsive genes continue to be expressed in men that were thought to be androgen insensitive. This implies that the AR signaling pathway continues to drive prostate cancer growth in the majority of patients. (Schweizer et al.)

Corticosteroids are also commonly used in the treatment of mCRPC, partly because of their inhibitory effects on the secretion of adrenocorticotropic hormone (ACTH) and partly because of their palliative effects. Inhibition of ACTH results in a number of effects, such as the downregulation of adrenal androgens, transcription factors, and cytokines. In addition, corticosteroids may have a cytotoxic effect on prostate cancer cells, mediated in part by the downregulation of androgen receptors and the activation of glucocorticoid receptor-mediated signaling and downstream antiangiogenic activity. (Maria De Santis et al., Practical Guidance on the Role of Corticosteroids in the Treatment of Metastatic Castration-resistant Prostate Cancer, *Urology*, Volume 96, October 2016, Pages 156-164). Abiraterone with prednisone or prednisolone is indicated for the treatment of mCRPC in patients who are chemotherapy-naïve, as well as those whose disease has progressed on or after a docetaxel-based chemotherapy regimen. Abiraterone plus prednisone was approved for the treatment of mCRPC patients. (Maria De Santis et al.).

Prostate cancer with DNA repair defects may also be vulnerable to therapeutic targeting by Poly(ADP-ribose) polymerase (PARP) inhibitors. PARP enzymes modify target proteins with ADP-ribose in a process called PARylation and are involved in single strand break repair. PARP inhibitors are considered to be a viable pathway to treat cancer by targeting the dependence of BRCA-mutant cancer cells on the PARP-associated repair pathway. Virtanen et al., PARP Inhibitors in Prostate Cancer—the Preclinical Rationale and Current Clinical Development, *Genes (Basel)*. 2019 August; 10(8): 565.

BET proteins are key regulators of AR signaling. BET protein regulate AR signaling both directly through regulation of androgen receptor expression and indirectly through regulation of downstream AR-target genes.

There continues to be a long felt need for improvements to the treatment of castration resistant prostate cancer. There has been much medical research effort in this field, and there continues to be tremendous ongoing efforts to improve drug therapies for treating castration resistant prostate cancer.

SUMMARY

The present disclosure relates to novel combination drug therapies useful for the treatment of cancer, such as prostate cancer. In one embodiment, the present disclosure relates to a method of treating a subject suffering from a cancer, comprising administering to the subject a combination of agents comprising:

(a) Compound I:

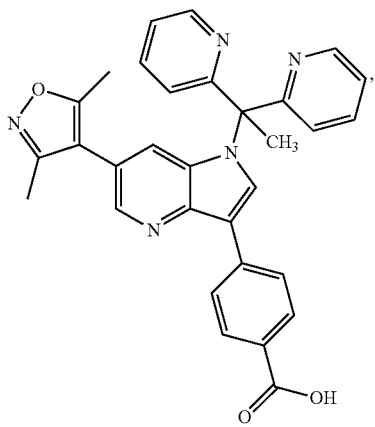

or a pharmaceutically acceptable salt thereof; and
(b) one or more inhibitors of the androgen receptor signaling pathway; or
(c) one or more PARP inhibitors;
wherein the amount of the combination of agents is therapeutically effective in the treatment.

In another embodiment, the present disclosure relates to a kit for use in the treatment of a cancer comprising a first component which comprises Compound I:
(a) Compound I:

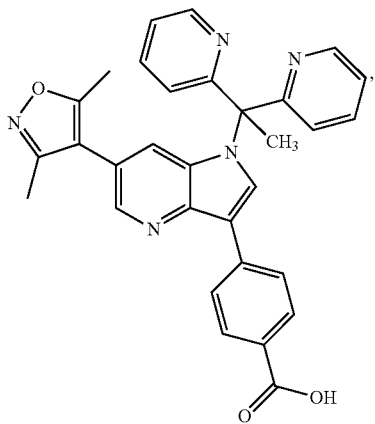

or a pharmaceutically acceptable salt thereof; and
(b) one or more inhibitors of the androgen receptor signaling pathway; or
(c) one or more PARP inhibitors.

Additional embodiments will be apparent from the following Drawings and Detailed Description and from the claims.

BRIEF DESCRIPTION OF THE DRAWINGS

FIGS. 2A, 2B, 2C, and 2D illustrate a combination of Compound I and enzalutamide exhibit synergistic inhibition of LNCaP cell growth: FIG. 2B illustrates Loewe interaction analyses using the Combenefit software of combination concentrations of Compound I and enzalutamide, or Compound I; FIG. 2A values are percentage control; FIG. 2C illustrates combination dose-responsive curves with respect to Compound I and enzalutamide for LNCaP cells; and FIG. 2D shows the Combination Index (CI) values at $ED_{50}$, $ED_{75}$, and $ED_{95}$ are 0.63, 0.64 and 0.72 for LNCaP cells.

FIGS. 3A, 3B, 3C, and 3D illustrate a combination of Compound I and enzalutamide exhibit synergistic inhibition of 22RV1 Cell Growth: FIG. 3B illustrates Loewe interaction analyses using the Combenefit software of combination concentrations of Compound I and enzalutamide, or Compound I; FIG. 3A values are percentage control; FIG. 3C illustrates combination dose-responsive curves with respect to Compound I and enzalutamide for 22Rv1 cells; and FIG. 3D shows the Combination Index (CI) values at $ED_{50}$, $ED_{75}$, and $ED_{95}$ are 0.63, 0.64 and 0.72 for 22Rv1 cells.

FIGS. 4A, 4B, 4C, and 4D illustrate a combination of Compound I and abiraterone acetate exhibit synergistic inhibition of LNCaP Cell Growth: FIG. 4B illustrates Loewe interaction analyses using the Combenefit software of many combination concentrations of Compound I and abiraterone acetate, or Compound I; FIG. 4A values are percentage control; FIG. 4C illustrates combination dose-responsive curves with respect to Compound I and enzalutamide for LNCaP cells; and FIG. 4D shows the Combination Index (CI) values at $ED_{50}$, $ED_{75}$, and $ED_{95}$ are 0.63, 0.64 and 0.72 for LNCaP cells.

FIGS. 5A, 5B, 5C, and 5D illustrate a combination of Compound I and abiraterone acetate exhibit synergistic inhibition of 22Rv1 Cell Growth: FIG. 5B illustrates a Loewe interaction analyses using the Combenefit software of many combination concentrations of Compound I and enzalutamide, or Compound I; FIG. 5A values are percentage control; FIG. 5C illustrates combination dose-responsive curves with respect to Compound I and enzalutamide for 22Rv1 cells; and FIG. 5D shows the Combination Index (CI) values at $ED_{50}$, $ED_{75}$, and $ED_{95}$ are 0.63, 0.64 and 0.72 for 22Rv1 cells.

FIG. 6A illustrates one partial response that was achieved after 9 cycles (each cycle is of 21 days) with 37.5% reduction in target lesions when treated with 40 mg QD of Compound I in combination with 1000 mg QD of abiraterone acetate and 5 mg BID prednisone. FIG. 6A also illustrates that one stable disease was achieved after 3 cycles with 10.3% increase in target lesions. FIG. 6B shows the spider plot % change in target lesions for the two human patients. FIG. 6A also illustrates that the third human patient when treated with 80 mg QD of Compound I in combination with 1000 mg QD of abiraterone acetate and 5 mg BID prednisone, did not have baseline response assessment.

FIG. 7A illustrates that stable disease was achieved after 2 cycles (each cycle is of 21 days) and was confirmed after 6 cycles with 25.4% reduction in target lesions when the patient was treated with 20 mg QD of Compound I in combination with 300 mg BID olaparib. FIG. 7B shows the spider plot % change in target lesions for the patient.

DETAILED DESCRIPTION

Figure 1A:
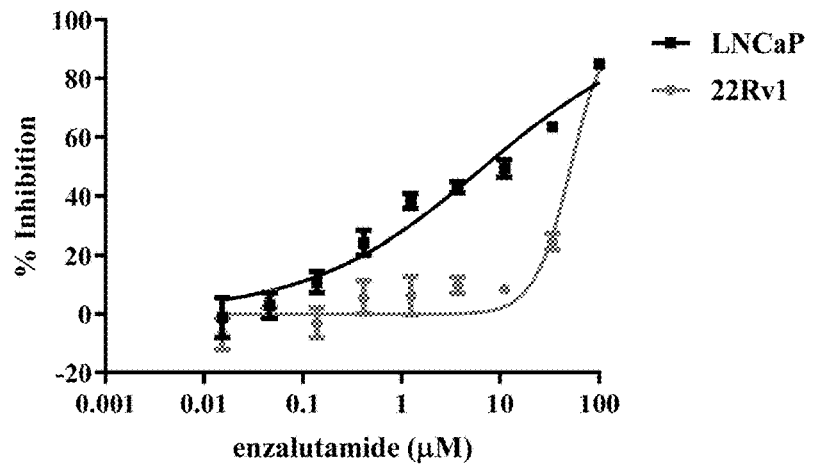
FIGS. 1A, 1B, and 1C illustrate $IC_{50}$ for Compound I, enzalutamide and abiraterone acetate, and the differential sensitivity of enzalutamide and abiraterone acetate to LNCaP and 22Rv1 cells as provided in Table 1.

The compound 4-(1-(1,1-di(pyridin-2-yl)ethyl)-6-(3,5-dimethylisoxazol-4-yl)-1H-pyrrolo[3,2-b]pyridin-3-yl)benzoic acid, designated herein as Compound I or Compound I (free acid), has the following formula:

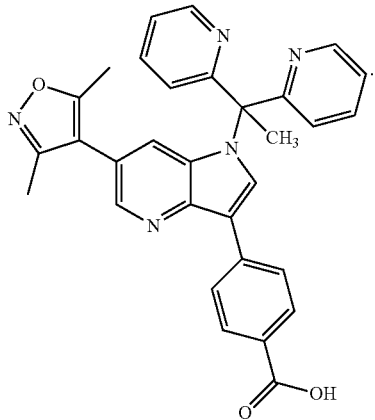

Compound I

Compound I is an inhibitor or modulator of bromodomain proteins. The synthesis and method of use thereof is described in U.S. Pat. Nos. 9,771,363, 9,975,894, 10,370,374, and 10,647,716, each of which is herein incorporated by reference in its entirety.

Definitions

As used in the present specification, the following words and phrases are generally intended to have the meanings as set forth below, except to the extent that the context in which they are used indicates otherwise.

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds, and reference to "the assay" includes reference to one or more assays and equivalents thereof known to those skilled in the art.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X".

Recitation of numeric ranges of values throughout the disclosure is intended to serve as a shorthand notation of referring individually to each separate value falling within the range inclusive of the values defining the range, and each separate value is incorporated in the specification as it were individually recited herein.

Any formula or structure given herein, including Compound I, is also intended to represent unlabeled forms as well as isotopically labeled forms of the compounds. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^{1}H$, $^{2}H$, $^{3}H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

As used herein, the terms "treat," "treating," "therapy," "therapies," and like terms refer to the administration of material, e.g., any one or more solid, crystalline or polymorphs of Compound I as described herein in an amount effective to prevent, alleviate, or ameliorate one or more symptoms of a disease or condition, i.e., indication, and/or to prolong the survival of the subject being treated.

The term "administering," "administered," or "taken" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. "Administered to the subject" is meant to also mean "taken by the subject."

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration (e.g., as $IC_{50}$) or effective concentration (e.g., as $EC_{50}$) of the compound for an inhibitor or activator, respectively, with respect to, for example, an enzyme. administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats. In another embodiment, the subject as used throughout the specification is a patient.

The term "pharmaceutically acceptable" indicates that the indicated material does not have properties that would cause a reasonably prudent medical practitioner to avoid administration of the material to a subject taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. The therapeutically effective amount will vary depending on the compound(s) along with any co-administered treatments, the nature of the disorder or condition and its course and severity, and the age, weight, etc., of the mammal to be treated. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. The effective amount of a compound in combination may be less than that of the same compound administered alone.

The terms "cancer" and "cancerous" refer to or describe the physiological condition in mammals that is typically characterized by unregulated cell growth/proliferation. Examples of cancer include, but are not limited to, prostate cancer (including castration resistant prostate cancer and metastatic castration resistant prostate cancer) and ovarian cancer.

"Bromodomain Inhibition" means decreasing a cell's growth or proliferation by at least 10%, 20%, 30%, 40%, 50%, 60%, 70%, 80%, 90%, 95%, or 100%, and includes inducing cell death, by of modulation of a bromodomain.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The term "castration resistant prostate cancer" (or "CRPC") refers to or describes prostate cancer in which a subject is resistant to castration or medication administered to effect castration (e.g., an anti-androgen therapy such as abiraterone). CRPC encompasses both castration resistant patients and patients with castration sensitive prostate cancer who receive an initial abiraterone treatment (or another anti-androgen therapy) and become castration resistant upon developing prostate-specific antigen (PSA) progression on abiraterone (or the anti-androgen therapy). The term is also meant to include metastatic forms of CRPC.

EMBODIMENTS

Embodiment 1 of this disclosure relates to a method of treating a subject suffering from a cancer, comprising administering to the subject a combination of agents comprising:

(a) Compound I:

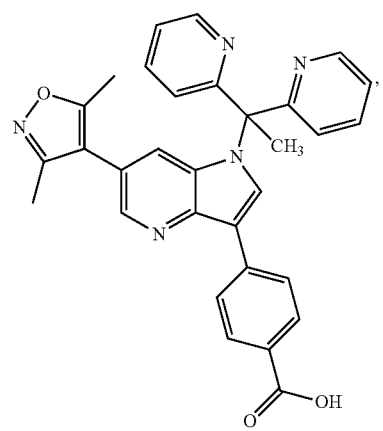

or a pharmaceutically acceptable salt thereof; and
(b) one or more inhibitors of the androgen receptor signaling pathway; or
(c) one or more PARP inhibitors;
wherein the amount of the combination of agents is therapeutically effective in the treatment.

Embodiment 2 of this disclosure relates to Embodiment 1, wherein the cancer is castration resistant prostate cancer.

Embodiment 3 of this disclosure relates to Embodiment 2, wherein the cancer is metastatic castration resistant prostate cancer.

Embodiment 4 of this disclosure relates to Embodiment 2 or 3, wherein the subject is a human.

Embodiment 5 of this disclosure relates to any of Embodiments 2 to 4 in which Compound I, or a pharmaceutically acceptable salt thereof, is administered in tablet form.

Embodiment 6 of this disclosure relates to any of Embodiments 2 to 5, wherein the subject is administered Compound I with one or more inhibitors of the androgen receptor signaling pathway comprising one or more cytochrome P450-17A1 inhibitors independently selected from the group consisting of abiraterone, abiraterone acetate, ketoconazole, seviteronel, orteronel, galeterone, and CFG920 (from Novartis), or a pharmaceutically acceptable salt thereof.

Embodiment 7 of this disclosure relates to Embodiment 6, wherein the cytochrome P450-17A1 inhibitor is abiraterone or abiraterone acetate.

Embodiment 8 of this disclosure relates to Embodiment 6, wherein the cytochrome P450-17A1 inhibitor is abiraterone acetate.

Embodiment 9 of this disclosure relates to any one of Embodiments 6 to 8 further comprising administering a corticosteroid, wherein the amount of the combination of agents is therapeutically effective in the treatment.

Embodiment 10 of this disclosure relates to Embodiment 9, wherein the corticosteroid is prednisone or prednisolone.

Embodiment 10a of this disclosure relates to Embodiment 10, wherein the corticosteroid is prednisone.

Embodiment 10b of this disclosure relates to Embodiment 10, wherein the corticosteroid is prednisolone.

Embodiment 11 of this disclosure relates to any one of Embodiments 2 to 5, wherein the subject is administered Compound I with one or more PARP inhibitors.

Embodiment 12 of this disclosure relates to Embodiment 11, wherein the one or more PARP inhibitors are independently selected from the group consisting of olaparib, niraparib, rucaparib, talazoparib, and veliparib, or a pharmaceutically acceptable salt thereof.

Embodiment 13 of this disclosure relates to Embodiment 12, wherein the PARP inhibitor is olaparib or a pharmaceutically acceptable salt thereof.

Embodiment 14 of this disclosure relates to any one of Embodiments 2 to 13, wherein Compound I, or a pharmaceutically acceptable salt thereof, is administered in an amount of from about 5 mg/day to about 200 mg/day.

Embodiment 15 of this disclosure relates to Embodiment 14, wherein Compound I, or a pharmaceutically acceptable salt thereof, is administered in an amount of from about 10 mg/day to about 100 mg/day.

Embodiment 16 of this disclosure relates to Embodiment 15, wherein Compound I, or a pharmaceutically acceptable salt thereof, is administered in an amount of from about 20 mg/day to about 80 mg/day.

Embodiment 17 of this disclosure relates to Embodiment 10, wherein Compound I, or a pharmaceutically acceptable salt thereof, is administered in an amount of from about 5 mg/day to about 200 mg/day; abiraterone acetate is administered in an amount of from about 500 mg/day to about 1500 mg/day; and prednisone or prednisolone is administered in an amount of from about 2 mg/day to about 40 mg/day.

Embodiment 17a of this disclosure relates to Embodiment 17, wherein Compound I, or a pharmaceutically acceptable salt thereof, is administered in an amount of from about 5 mg/day to about 200 mg/day; abiraterone acetate is administered in an amount of from about 500 mg/day to about 1500 mg/day; and prednisone is administered in an amount of from about 2 mg/day to about 40 mg/day.

Embodiment 17b of this disclosure relates to Embodiment 17, wherein Compound I, or a pharmaceutically acceptable salt thereof, is administered in an amount of from about 5 mg/day to about 200 mg/day; abiraterone acetate is administered in an amount of from about 500 mg/day to about 1500 mg/day; and prednisolone is administered in an amount of from about 2 mg/day to about 40 mg/day.

Embodiment 18 of this disclosure relates to Embodiment 17, wherein Compound I, or a pharmaceutically acceptable salt thereof, is administered in an amount of from about 10 mg/day to about 100 mg/day; abiraterone acetate is administered in an amount of from about 750 mg/day to about 1250 mg/day; and prednisone or prednisolone is administered in an amount of from about 5 mg/day to about 20 mg/day.

Embodiment 18a of this disclosure relates to Embodiment 18, wherein Compound I, or a pharmaceutically acceptable salt thereof, is administered in an amount of from about 10 mg/day to about 100 mg/day; abiraterone acetate is administered in an amount of from about 750 mg/day to about 1250 mg/day; and prednisone is administered in an amount of from about 5 mg/day to about 20 mg/day.

Embodiment 18b of this disclosure relates to Embodiment 18, wherein Compound I, or a pharmaceutically acceptable salt thereof, is administered in an amount of from about 10 mg/day to about 100 mg/day; abiraterone acetate is administered in an amount of from about 750 mg/day to about 1250 mg/day; and prednisolone is administered in an amount of from about 5 mg/day to about 20 mg/day.

Embodiment 19 of this disclosure relates to Embodiment 18, wherein Compound I, or a pharmaceutically acceptable salt thereof, is administered in an amount of from about 20 mg/day to about 80 mg/day; abiraterone acetate is administered in an amount of about 1000 mg/day; and prednisone or prednisolone is administered in an amount of about 10 mg/day.

Embodiment 19a of this disclosure relates to Embodiment 19, wherein Compound I, or a pharmaceutically acceptable salt thereof, is administered in an amount of from about 20 mg/day to about 80 mg/day; abiraterone acetate is administered in an amount of about 1000 mg/day; and prednisone is administered in an amount of about 10 mg/day.

Embodiment 19b of this disclosure relates to Embodiment 19, wherein Compound I, or a pharmaceutically acceptable salt thereof, is administered in an amount of from about 20 mg/day to about 80 mg/day; abiraterone acetate is administered in an amount of about 1000 mg/day; and prednisolone is administered in an amount of about 10 mg/day.

Embodiment 20 of this disclosure relates to Embodiment 19, wherein Compound I, or a pharmaceutically acceptable salt thereof, is administered in an amount of from about 20 mg/day to about 80 mg/day; 1000 mg abiraterone acetate are administered orally once daily; and 5 mg prednisone or prednisolone are administered orally twice daily.

Embodiment 20a of this disclosure relates to Embodiment 20, wherein Compound I, or a pharmaceutically acceptable salt thereof, is administered in an amount of from about 20 mg/day to about 80 mg/day; 1000 mg abiraterone acetate are administered orally once daily; and 5 mg prednisone are administered orally twice daily.

Embodiment 20b of this disclosure relates to Embodiment 20, wherein Compound I, or a pharmaceutically acceptable salt thereof, is administered in an amount of from about 20 mg/day to about 80 mg/day; 1000 mg abiraterone acetate are administered orally once daily; and 5 mg prednisolone are administered orally twice daily.

Embodiment 21 of this disclosure relates to Embodiment 20, wherein prednisone or prednisolone is taken at least 2 hours before Compound I and abiraterone acetate or 1 hour after taking Compound I and abiraterone acetate.

Embodiment 22 of this disclosure relates to any one of Embodiments 17 to 21, wherein the cancer is metastatic castration resistant prostate cancer, and wherein the treatment is initiated after the subject with metastatic castration resistant prostate cancer develops disease progression while concurrently receiving treatment with abiraterone acetate and prednisone or prednisolone.

Embodiment 23 of this disclosure relates to any one of Embodiments 7, 8, 9, 14, 15, 16, 17, 18, 19, 20, 21, or 22, wherein Compound I and abiraterone acetate are administered to the subject at the same time.

Embodiment 24 of this disclosure relates to Embodiment 13, wherein Compound I, or a pharmaceutically acceptable salt thereof, is administered in an amount of from about 5 mg/day to about 200 mg/day; and olaparib, or a pharmaceutically acceptable salt thereof, is administered in an amount of from about 300 mg/day to about 900 mg/day.

Embodiment 25 of this disclosure relates to Embodiment 24, wherein Compound I, or a pharmaceutically acceptable salt thereof, is administered in an amount of from about 10 mg/day to about 100 mg/day; and olaparib, or a pharmaceutically acceptable salt thereof, is administered in an amount of from about 500 mg/day to about 700 mg/day.

Embodiment 26 of this disclosure relates to Embodiment 25, wherein Compound I, or a pharmaceutically acceptable salt thereof, is administered in an amount of from about 20 mg/day to about 80 mg/day; and olaparib, or a pharmaceutically acceptable salt thereof, is administered in an amount of about 600 mg/day.

Embodiment 27 of this disclosure relates to Embodiment 26, wherein 300 mg tablet of olaparib is orally administered to the subject twice daily.

Embodiment 28 of this disclosure relates to Embodiment 27, wherein a morning dose of olaparib is administered to the subject at the same time as Compound I.

Embodiment 29 of this disclosure relates to any one of Embodiments 24 to 28, wherein the subject has deleterious or suspected deleterious germline or somatic homologous recombination repair (HRR) gene-mutated metastatic castration-resistant prostate cancer.

Embodiment 30 of this disclosure relates to any one of Embodiments 24 to 29, wherein the cancer is metastatic castration resistant prostate cancer and the treatment is initiated after the subject with metastatic castration resistant prostate cancer develops disease progression after treatment with either abiraterone acetate and prednisone or after treatment with enzalutamide.

Embodiment 31 of this disclosure relates to Embodiment 1, wherein the cancer is ovarian cancer, the subject is a human, and wherein the human is administered Compound I and one or more PARP inhibitors.

Embodiment 31a of this disclosure relates to Embodiment 31, wherein the dosage amounts of PARP, and the dosage amounts of Compound I, are those in any embodiment in this disclosure.

Embodiment 32 of this disclosure relates to kit for use in the treatment of a cancer comprising a first component which comprises
(a) Compound I:

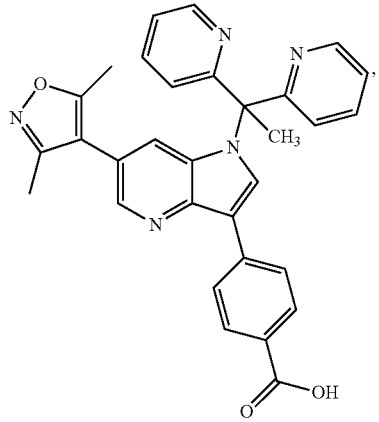

or a pharmaceutically acceptable salt thereof; and
(b) one or more inhibitors of the androgen receptor signaling pathway; or
(c) one or more PARP inhibitors.

Embodiment 33 of this disclosure relates to Embodiment 32, wherein the cancer is castration resistant prostate cancer.

Embodiment 34 of this disclosure relates to Embodiment 32, wherein the cancer is ovarian cancer.

Embodiment 35 of this disclosure relates to any one of Embodiments 2 to 5, wherein the subject is administered Compound I and enzalutamide, or a pharmaceutically acceptable salt thereof.

Embodiment 36 of this disclosure relates to Embodiment 35, wherein Compound I, or a pharmaceutically acceptable salt thereof, is administered in an amount of from about 5 mg/day to about 200 mg/day; and enzalutamide, or a pharmaceutically acceptable salt thereof, is administered in an amount of from about 10 mg/day to about 500 mg/day.

Embodiment 37 of this disclosure relates to Embodiment 36, wherein Compound I, or a pharmaceutically acceptable salt thereof, is administered in an amount of from about 10 mg/day to about 100 mg/day; and enzalutamide, or a pharmaceutically acceptable salt thereof, is administered in an amount of from about 20 mg/day to about 400 mg/day.

Embodiment 38 of this disclosure relates to Embodiment 37, wherein Compound I, or a pharmaceutically acceptable salt thereof, is administered in an amount of from about 20 mg/day to about 80 mg/day; and enzalutamide, or a pharmaceutically acceptable salt thereof, is administered in an amount of from about 40 mg/day to about 240 mg/day.

Embodiment 39 of this disclosure relates to Embodiment 38, wherein Compound I, or a pharmaceutically acceptable salt thereof, is administered in an amount of from about 20 mg/day to about 80 mg/day; and enzalutamide is administered in an amount of about 160 mg/day.

Embodiment 40 of this disclosure relates to a method of treating a subject suffering from a cancer, comprising administering to the subject a combination of agents comprising:
(a) Compound I:

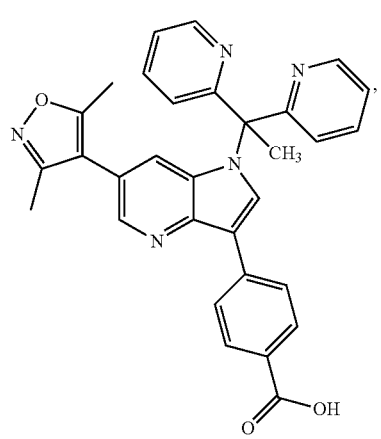

or a pharmaceutically acceptable salt thereof;
(b) one or more inhibitors of the androgen receptor signaling pathway; and
(c) one or more PARP inhibitors;
wherein the amount of the combination of agents is therapeutically effective in the treatment.

Embodiment 41 of this disclosure relates to Embodiment 40, wherein the cancer is castration resistant prostate cancer.

Embodiment 42 of this disclosure relates to Embodiment 41, wherein the cancer is metastatic castration resistant prostate cancer.

Embodiment 43 of this disclosure relates to Embodiment 40, wherein the cancer is ovarian cancer.

Embodiment 44 of this disclosure relates to any of Embodiments 41-43, wherein the subject is a human.

Embodiment 45 of this disclosure relates to any of Embodiments 40-44 in which Compound I, or a pharmaceutically acceptable salt thereof, is administered in tablet form.

Embodiment 46 of this disclosure relates to any of Embodiments 40-45, wherein the one or more inhibitors of the androgen receptor signaling pathway comprise one or more cytochrome P450-17A1 inhibitors independently selected from the group consisting of abiraterone, abiraterone acetate, ketoconazole, seviteronel, orteronel, galeterone, and CFG920 (from Novartis), or a pharmaceutically acceptable salt thereof.

Embodiment 47 of this disclosure relates to Embodiment 46, wherein the cytochrome P450-17A1 inhibitor is abiraterone or abiraterone acetate.

Embodiment 48 of this disclosure relates to Embodiment 47, wherein the cytochrome P450-17A1 inhibitor is abiraterone acetate.

Embodiment 49 of this disclosure relates to any one of Embodiments 46-48 further comprising administering a corticosteroid, wherein the amount of the combination of agents is therapeutically effective in the treatment.

Embodiment 50 of this disclosure relates to Embodiment 49, wherein the corticosteroid is prednisone or prednisolone.

Embodiment 51 of this disclosure relates to Embodiment 50, wherein the corticosteroid is prednisone.

Embodiment 52 of this disclosure relates to Embodiment 50, wherein the corticosteroid is prednisolone.

Embodiment 53 of this disclosure relates to any one of Embodiments 40-52, wherein the one or more PARP inhibitors are independently selected from the group consisting of olaparib, niraparib, rucaparib, talazoparib, and veliparib, or a pharmaceutically acceptable salt thereof.

Embodiment 54 of this disclosure relates to Embodiment 53, wherein the PARP inhibitor is olaparib or a pharmaceutically acceptable salt thereof.

Embodiment 55 of this disclosure relates to a method of treating a subject suffering from a cancer, comprising administering to the subject a combination of agents comprising:

(a) Compound I:

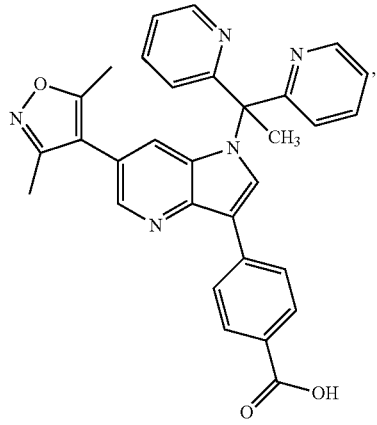

or a pharmaceutically acceptable salt thereof;
(b) abiraterone acetate; and
(c) olaparib or a pharmaceutically acceptable salt thereof, wherein the amount of the combination of agents is therapeutically effective in the treatment.

Embodiment 56 of this disclosure relates to Embodiments 55 further comprising administering a corticosteroid, wherein the amount of the combination of agents is therapeutically effective in the treatment.

Embodiment 57 of this disclosure relates to Embodiment 56, wherein the corticosteroid is prednisone or prednisolone.

Embodiment 58 of this disclosure relates to Embodiment 57, wherein the corticosteroid is prednisone.

Embodiment 59 of this disclosure relates to Embodiment 57, wherein the corticosteroid is prednisolone.

Embodiment 60 of this disclosure relates to Embodiment 55, wherein Compound I, or a pharmaceutically acceptable salt thereof, is administered in an amount of from about 5 mg/day to about 200 mg/day; abiraterone acetate is administered in an amount of from about 500 mg/day to about 1500 mg/day; and olaparib, or a pharmaceutically acceptable salt thereof, is administered in an amount of from about 300 mg/day to about 900 mg/day.

Embodiment 61 of this disclosure relates to Embodiment 59, wherein Compound I, or a pharmaceutically acceptable salt thereof, is administered in an amount of from about 5 mg/day to about 200 mg/day; abiraterone acetate is administered in an amount of from about 500 mg/day to about 1500 mg/day; olaparib, or a pharmaceutically acceptable salt thereof, is administered in an amount of from about 300 mg/day to about 900 mg/day; and prednisolone is administered in an amount of from about 2 mg/day to about 40 mg/day.

Embodiment 62 of this disclosure relates to any one of Embodiments 40-45, wherein the one or more inhibitors of the androgen receptor signaling pathway comprises enzalutamide and the PARP inhibitor is olaparib.

Embodiment 63 of this disclosure relates to Embodiment 62, wherein Compound I, or a pharmaceutically acceptable salt thereof, is administered in an amount of from about 5 mg/day to about 200 mg/day; enzalutamide is administered in an amount of from about 500 mg/day to about 1500 mg/day; and olaparib, or a pharmaceutically acceptable salt thereof, is administered in an amount of from about 300 mg/day to about 900 mg/day.

Embodiment 64 of this disclosure relates to Embodiment 63, further comprising prednisolone administered in an amount of from about 2 mg/day to about 40 mg/day.

Embodiment 65 of this disclosure relates to use of a combination of agents comprising:
(a) Compound I:

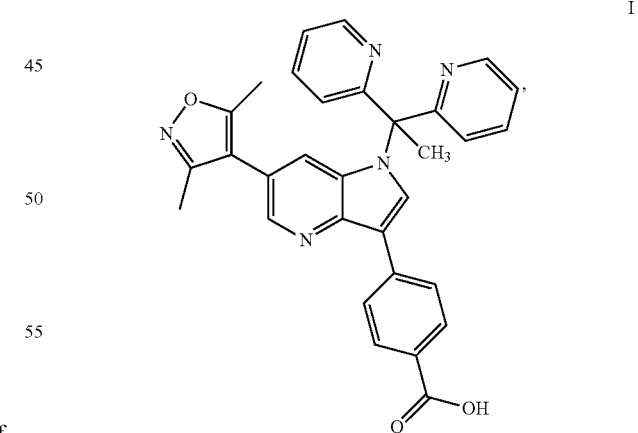

or a pharmaceutically acceptable salt thereof; and
(b) one or more inhibitors of the androgen receptor signaling pathway; or
(c) one or more PARP inhibitors;
for the treatment of cancer in a subject, wherein the amount of the combination of agents is therapeutically effective in the treatment.

Embodiment 66 of this disclosure relates to use of a combination of agents comprising:

(a) Compound I:

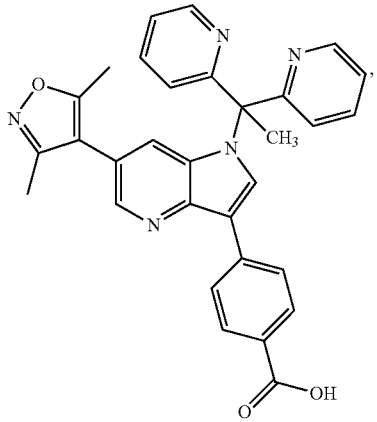

or a pharmaceutically acceptable salt thereof; and (b) one or more inhibitors of the androgen receptor signaling pathway; or (c) one or more PARP inhibitors, in the manufacture of a medicament for the treatment of cancer in a subject, wherein the amount of the combination of agents is therapeutically effective in the treatment.

Embodiment 67 of this disclosure relates to Embodiment 65 or 66, wherein the one or more inhibitors of the androgen receptor signaling pathway is abiraterone acetate.

Embodiment 68 of this disclosure relates to Embodiment 65 or 66, wherein the one or more PARP inhibitors is olaparib or a pharmaceutically acceptable salt thereof.

Embodiment 69 of this disclosure relates to Embodiment 67 or 68, wherein the combination of agents further comprises a corticosteroid.

Embodiment 70 of this disclosure relates to Embodiment 69, wherein the corticosteroid is prednisone or prednisolone.

Embodiment 71 of this disclosure relates to use of a combination of agents comprising:

(a) Compound I:

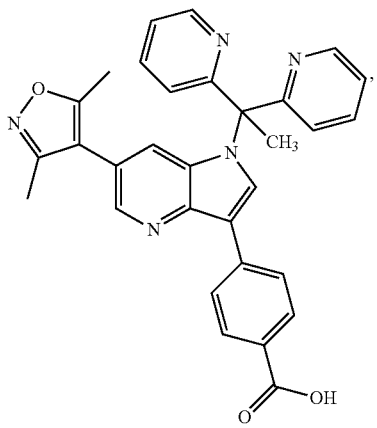

or a pharmaceutically acceptable salt thereof;

(b) one or more inhibitors of the androgen receptor signaling pathway; and (c) one or more PARP inhibitors, for the treatment of cancer in a subject, wherein the amount of the combination of agents is therapeutically effective in the treatment.

Embodiment 72 of this disclosure relates to use of a combination of agents comprising:

(a) Compound I:

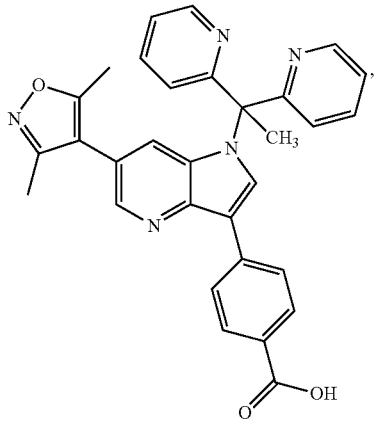

or a pharmaceutically acceptable salt thereof;

(b) one or more inhibitors of the androgen receptor signaling pathway; and (c) one or more PARP inhibitors, in the manufacture of a medicament for the treatment of cancer in a subject, wherein the amount of the combination of agents is therapeutically effective in the treatment.

Embodiment 73 of this disclosure relates to Embodiment 71 or 72, wherein the one or more inhibitors of the androgen receptor signaling pathway is abiraterone acetate.

Embodiment 74 of this disclosure relates to Embodiment 71 or 72, wherein the one or more PARP inhibitors is olaparib or a pharmaceutically acceptable salt thereof.

Embodiment 75 of this disclosure relates to Embodiment 71 or 72, wherein the tone or more inhibitors of the androgen receptor signaling pathway is abiraterone acetate and the one or more PARP inhibitors is olaparib or a pharmaceutically acceptable salt thereof.

Embodiment 76 of this disclosure relates to Embodiment 75, wherein the combination of agents further comprises a corticosteroid.

Embodiment 77 of this disclosure relates to Embodiment 76, wherein the corticosteroid is prednisone or prednisolone.

Embodiment 78 of this disclosure relates to a method of treating a subject suffering from a cancer, comprising administering to the subject a combination of agents comprising:

(a) Compound I:

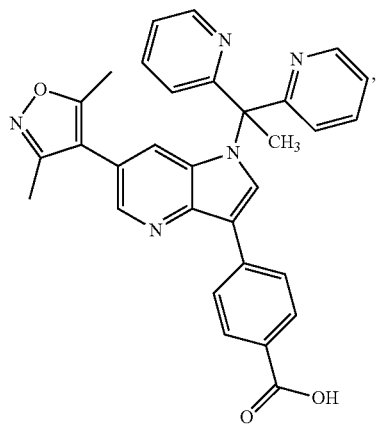

or a pharmaceutically acceptable salt thereof;
(b) abiraterone acetate; and
(c) olaparib or a pharmaceutically acceptable salt thereof,
wherein the amount of the combination of agents is therapeutically effective in the treatment.

The amount of each agent administered according to the present method may, but does not have to be therapeutically effective by itself. That is, the present disclosure contemplates combinations wherein the amount of Compound I, or a pharmaceutically acceptable salt thereof, and/or the amount of other agents in the combination may be less than the amount that is therapeutically effective for each active agent when said agent is administered in monotherapy.

In another embodiment of the present disclosure, the administration of Compound I, or a pharmaceutically acceptable salt thereof, occurs until disease progression or unacceptable toxicity.

In another aspect of this disclosure, the agents herein described above are administered in conjunction with radiotherapy and/or in conjunction with another active agent.

Each agent (e.g., Compound I, one or more inhibitors of the androgen receptor signaling pathway optionally with prednisone, a PARP), may also be a component of a composition including additional components such as preserving agents, solubilizing agents, stabilizing agents, wetting agents, emulsifying agents, sweetening agents, coloring agents, flavoring agents, salts for varying the osmotic pressure, buffers, coating agents and antioxidants.

Administration
Compound I Administration

In any embodiment described herein, a tablet or capsule form of Compound I for oral use can comprise 1-100 mg of Compound I. In other embodiments, a tablet or capsule form of Compound for oral use I can comprise 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg of Compound I. In other embodiments, 20 mg of Compound I is administered to the subject daily in 5 mg, 10 mg, 15 mg, or 20 mg tablets for oral use. In other embodiments, 30 mg of Compound I is administered to the subject daily in 5 mg, 10 mg, 15 mg, 20 mg, 25 mg, or 30 mg tablets for oral use. In other embodiments, 40 mg of Compound I is administered to the subject daily in 5 mg, 10 mg, 15 mg, 20 mg, 25 mg, 30 mg, 35 mg, or 40 mg tablets for oral use. In other embodiments, 50 mg of Compound I is administered to the subject daily by the subject in 5 mg, 10 mg, 15 mg, 20 mg, 25 mg, 30 mg, 35 mg, 40 mg, 45 mg, or 50 mg tablets for oral use. In other embodiments, 60 mg of Compound I is administered to the subject daily in 5 mg, 10 mg, 15 mg, 20 mg, 25 mg, 30 mg, 35 mg, 40 mg, 45 mg, 50 mg, 55 mg, or 60 mg tablets for oral use. In other embodiments, 50 mg of Compound I is administered to the subject daily in 5 mg, 10 mg, 15 mg, 20 mg, 25 mg, 30 mg, 35 mg, 40 mg, 45 mg, or 50 mg tablets for oral use. In other embodiments, 70 mg of Compound I is administered to the subject daily in 5 mg, 10 mg, 15 mg, 20 mg, 25 mg, 30 mg, 35 mg, 40 mg, 45 mg, 50 mg, 55 mg, 60 mg, 65 mg, or 70 mg tablets for oral use. In other embodiments, 80 mg of Compound I is administered to the subject daily in 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, or 80 mg tablets for oral use. In other embodiments, tablets of Compound I, in any of the dosage strengths described in this disclosure, is administered orally with water. In other embodiments, Compound I is administered as a tablet whole and not crushed, chewed or dissolved in water. In other embodiments, dosing period can be up to 30 minutes for the number of tablets to be administered to the subject. In other embodiments, any of the daily dosages of Compound I can be administered to the subject all at once or divided into several smaller dosages throughout the day. In another embodiment, a tablet containing 20 mg of Compound I is orally administered to the subject once daily. In another embodiment, 40 mg of Compound I is administered to the subject by orally administering two tablets containing 20 mg of Compound I once daily. In another embodiment, 40 mg of Compound I is administered to the subject daily by orally administering a tablet containing 20 mg of Compound I twice daily (i.e. 40 mg bid). In another embodiment, 80 mg of Compound I is administered to the subject daily by orally administering four tablets containing 20 mg of Compound I once daily. In another embodiment, 80 mg of Compound I is administered to the subject daily by administering two tablets containing 20 mg of Compound I twice daily (i.e., 80 mg bid).

Abiraterone Acetate Administration

In another embodiment, abiraterone acetate is administered to the subject on an empty stomach where no food is consumed for at least 2 hours before the dose of abiraterone acetate is taken and for at least 1 hour after the dose of abiraterone acetate is taken. In another embodiment, the tablets of abiraterone acetate are swallowed whole with water and not crushed or chewed. In another embodiment, the method comprises 1000 mg abiraterone acetate administered orally once daily in combination with prednisone 5 mg administered orally twice daily. Abiraterone acetate (ZYTIGA® or generic equivalent) is available as either 500 mg film-coated tablets or 250 mg uncoated tablets. Abiraterone acetate must be taken on an empty stomach. No food should be consumed for at least 2 hours before the dose of abiraterone acetate is taken and for at least 1 hour after the dose of abiraterone acetate is taken. The tablets should be swallowed whole with water and not be crushed or chewed. Please refer to the ZYTIGA® FDA label or SmPC for additional information. In another embodiment, Compound I and abiraterone acetate are taken at the same time.

Prednisone Administration

In one embodiment, prednisone 5 mg tablets are administered to the subject twice daily. In another embodiment, prednisone is taken with food or milk at least 2 hours before Compound I and abiraterone acetate or 1 hour after taking Compound I and abiraterone acetate. In other embodiments, other corticosteroids are used such as, without limitation, prednisolone.

Olaparib Administration

In one embodiment, a 300 mg tablet of olaparib is administered orally administered to the subject twice daily. In another embodiment, a morning dose of olaparib is administered to the subject at the same time as Compound I. In another embodiment, subjects fast for at least 2 hours before and 1 hour after taking Compound I and olaparib. In another embodiment, the evening olaparib dose is be taken with or without food. In other embodiments, olaparib is administered in the form of a tablet. In another embodiments, a tablet form of olaparib is swallowed whole with water and not chewed, crushed, dissolved, or divided.

Subject Dosing Embodiments

In one embodiment, 40 mg of Compound I is administered orally once daily in combination with abiraterone acetate 1000 mg administered orally once daily and prednisone 5 mg administered orally twice daily. In another embodiment, 40 mg of Compound I is administered orally once daily in combination with olaparib 300 mg administered orally twice daily. In another embodiment, 20 mg of Compound I is administered orally once daily in combination with abiraterone acetate 1000 mg administered orally once daily and prednisone 5 mg administered orally twice daily. In another embodiment, 20 mg of Compound I is administered orally once daily in combination with olaparib 300 mg administered orally twice daily. In another embodiment, 80 mg of Compound I is administered orally once daily in combination with abiraterone acetate 1000 mg administered orally once daily and prednisone 5 mg administered orally twice daily. In another embodiment, 80 mg of Compound I is administered orally once daily in combination with olaparib 300 mg administered orally twice daily.

EXAMPLES

The present disclosure will be more fully understood by reference to the following examples. They should not, however, be construed as limiting the scope of this disclosure.

Example 1

Compound Combination Studies of (A) Compound I and (B) Enzalutamide or Abiraterone Acetate in Prostate Cancer Cells Growth assays were done in triplicate and performed as follows.

1. On Day 1, LNCaP and 22Rv1 cells were seeded in wells of a 96-well plate at a density of 3000 cells/well in 100 μL of culture media (RPMI 1640 medium supplemented with 10% fetal bovine serum and 1% Penicillin/Streptomycin). Cells were incubated overnight at 37° C. in a humidified atmosphere with 5% $CO_2$.

2. On Day 2, for single compound treatment studies, each compound was serially diluted 1:3 in DMSO to create a 9-point titration. A 3 μL aliquot of each dilution was added to 747 μL culture media and 100 μL were added to each triplicate well. Wells containing 0.2% DMSO-treated cells served as uninhibited controls.

For the matrix combination studies, compounds at different maximal concentrations were serially diluted 1:3 in 100% DMSO to create a 6-point titration. In wells with two compounds ((A) Compound I and (B) enzalutamide or abiraterone acetate), a 1.4 μL volume of (A) and 1.4 μL of (B) in a series of six dilution concentrations were then added to wells containing 347.2 μL growth medium, resulting a 6×6 dose matrix. In wells with a single compound, a 1.4 μL volume of the single compound and 1.4 μL DMSO were added. In the control wells, 2.8 μL DMSO was added. A 100 μL volume of growth media containing single or both compounds or DMSO was added to wells containing cells. The final concentration of DMSO in all wells was 0.4%. DMSO treated cells served as the uninhibited control.

For the fixed-ratio combination study, combinations of two compounds ((A) Compound I and (B) enzalutamide or abiraterone acetate), in a fixed-ratio were evaluated. Compounds at different maximal concentrations were serially diluted 1:3 in 100% DMSO for a 9-point titration. In groups treated with a single compound, a 2 μL aliquot of each dilution point of Compound I or compound B (enzalutamide or abiraterone acetate) and 2 μL DMSO was added to wells containing 496 μL growth medium. In the combination treatment group, a 2 μL aliquot of each dilution point of Compound I and a 2 μL aliquot of Compound B were added to wells containing 496 μL growth medium. A 100 μL volume of growth media containing single or both compounds or DMSO were added to wells containing cells. The final concentration of DMSO in all wells was 0.4%. DMSO-treated cells served as the uninhibited control.

In all studies, cells were incubated at 37° C. in a humidified atmosphere with 5% $CO_2$ for 5 days.

3. On Day 7, cell cultures were brought to room temperature for 30 minutes and 50 μL of reconstituted CellTiter-Glo Reagent was added to each well. Plates were shaken at room temperature for approximately 15 minutes Luminescent signal was quantified on a microplate reader.

Data Analysis

1. For single compound treatment study, all responses were expressed as % inhibition (the percentage inhibition compared to the average response of the DMSO-treated control wells). The data were analyzed by using nonlinear regression to generate $IC_{50}$ values in Prism (GraphPad, La Jolla, Calif.). 95% confident interval ($CI_{95}$) of the $IC_{50}$ values were also calculated in Prism.

2. For synergy analysis of the fixed-ratio combination study, all responses were expressed as inhibition effect: the fraction inhibited compared to the mean response of the DMSO-treated control wells. Inhibition effects of single compound treatment and combination treatment and the compound doses were entered into CalcuSyn v2.1 (Biosoft, Cambridge, UK) to calculate combination index (CI) at $ED_{50}$, $ED_{75}$ and $ED_{90}$. CI offers a quantitative definition for different types of drug-drug interactions: nearly additive effect (CI=0.9-1.1), antagonism (CI>1.1), slight synergism (CI=0.85-0.9), moderate synergism (CI=0.7-0.85), synergism (CI=0.3-0.7), strong synergism (0.1-0.3), and very strong synergism (<0.1) (Chou 2006). The mean CI values with standard deviation were plotted (FIG. 2D, FIG. 3D, FIG. 4D and FIG. 5D).

3. For synergy analysis of the matrix combination study, all responses were expressed as % control (FIG. 2A, FIG. 3A, FIG. 4A and FIG. 5A) and data were processed and analyzed using Combenefit (Di Veroli 2016). Loewe (1953) model was used to measure synergy/antagonism levels. Score estimates additive effect (−5<score <5), synergism (score >5) and antagonism (score <−5). Statistical significance of the scores is determined by one-sample t-test (* p-value <5×10$^2$;  p-value <10$^3$; * p-value <10$^4$) in Combenefit.

Results:

Compound potency and effects were evaluated for Compound I in combination with enzalutamide and abiraterone acetate in LNCaP and 22Rv1 cells. The LNCaP cells express a mutant androgen receptor (AR-T877A) (Hara 2003). The 22Rv1 cells express both full-length AR (AR-FL) and AR-V7 (Li 2013). AR-V7 is responsible for androgen-independent growth and survival of 22Rv1 cells and confers resistance to enzalutamide (Li 2013) and abiraterone acetate (Liu 2016).

Figure 1B:
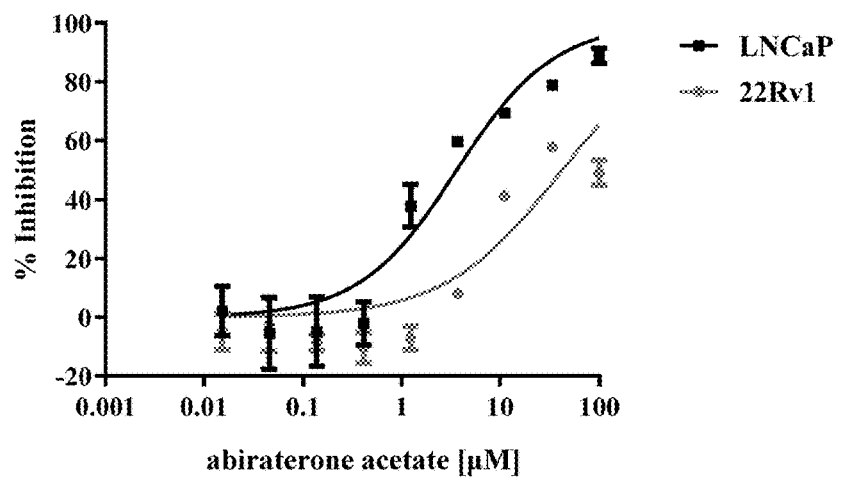
Figure 1C:
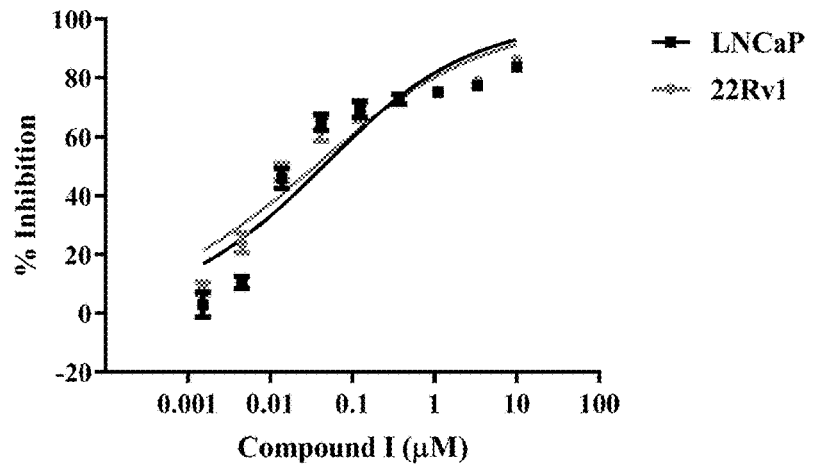

The $IC_{50}$ for each compound is shown in Table 1 and FIG. 1. Consistent with the literature, LNCaP and 22Rv1 cells exhibited differential sensitivity to enzalutamide and abiraterone acetate (Cai 2018; Hu 2015; Qi 2015). LNCaP cells were sensitive to growth inhibition by enzalutamide and abiraterone acetate with $IC_{50}$ of 6.8 and 3.5 μM, respectively, whereas 22Rv1 cells were more resistant to these compounds with $IC_{50}$ of 51 and 42 μM, respectively (Table 1 and FIG. 1). Compound I potently inhibited the growth of LNCaP and 22RV1 cells with $IC_{50}$ of 43 and 34 nM, respectively (Table 1 and FIG. 1).

A 6×6 dose-matrix combination study was performed in LNCaP and 22Rv1 cells which allows for systematic assessment of the effect of a broad range of combination concentrations for Compound I and enzalutamide, or Compound I and abiraterone acetate. The experimental data (FIG. 2A, FIG. 3A, FIG. 4A and FIG. 5A, values are percentage control) from the matrix combination study were analyzed with Loewe synergy models using the Combenefit software. Many combination concentrations of Compound I and enzalutamide, or Compound I and abiraterone acetate, were tested for synergy. Loewe interaction analyses suggests there can is additive (−5<score <5), antagonistic (score <−5) and synergistic (score >5) effects depending on the concentration of each compound used (FIG. 2B, FIG. 3B, FIG. 4B and FIG. 5B). Thus, Loewe interaction analyses suggests the synergy (score >5) between Compound I and enzalutamide or abiraterone acetate with LNCaP and 22Rv1 cells is a function of the specific combination concentrations of each agent.

Figure 2C:
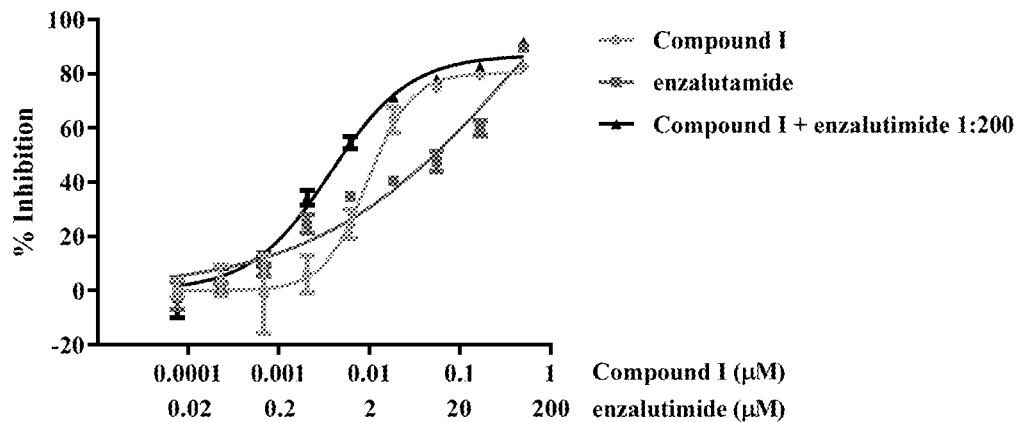
Figure 2D:
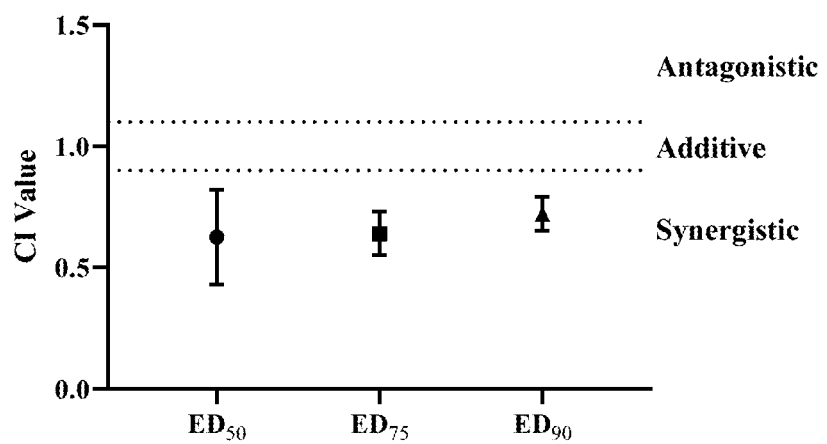
Figure 3C:
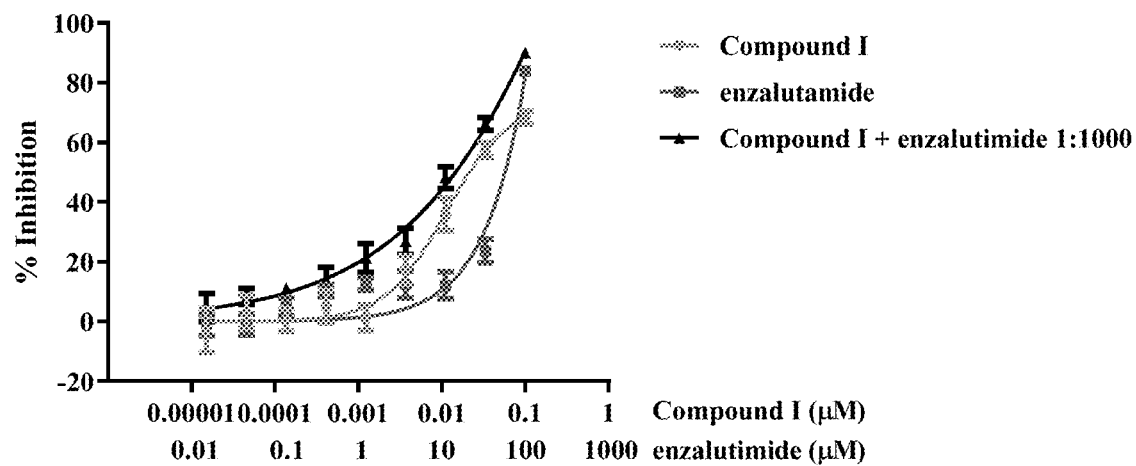
Figure 3D:
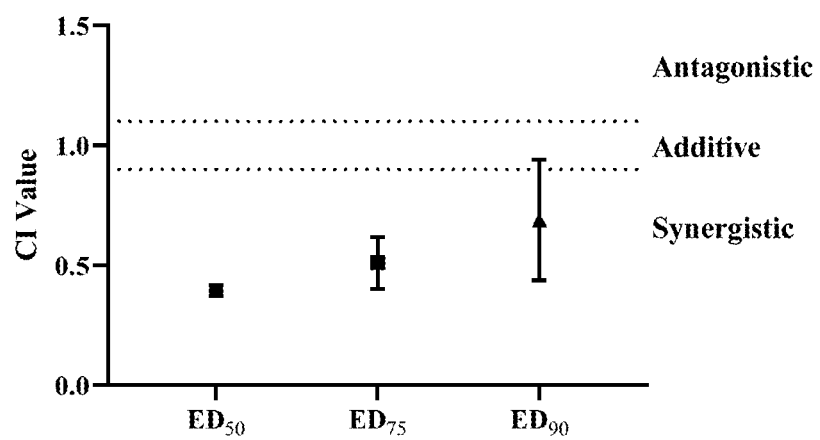

Based on compound $IC_{50}$ and data from matrix combination study, fixed ratio combination studies were designed in which two compounds were combined at constant ratios. Combinations of Compound I and enzalutamide at ratios of 1:200 in LNCaP cells and 1:1000 in 22Rv1 cells were evaluated. The combination dose-responsive curve was shifted to the left with respect to the two individual compound curves (FIG. 2C and FIG. 3C). Combination Index (CI) values at $ED_{50}$, $ED_{75}$, and $ED_{95}$ are 0.63, 0.64 and 0.72, respectively, for LNCaP cells, and 0.39, 0.51, 0.69, respectively, for 22Rv1 cells confirming the synergistic interaction between Compound I and enzalutamide in these cells (FIG. 2D and FIG. 3D). Combination index (CI) theorem offers quantitative definition for additive effect (CI=1), synergism (CI<1), and antagonism (CI>1) in drug combinations (Chou 2010).

Figure 4C:
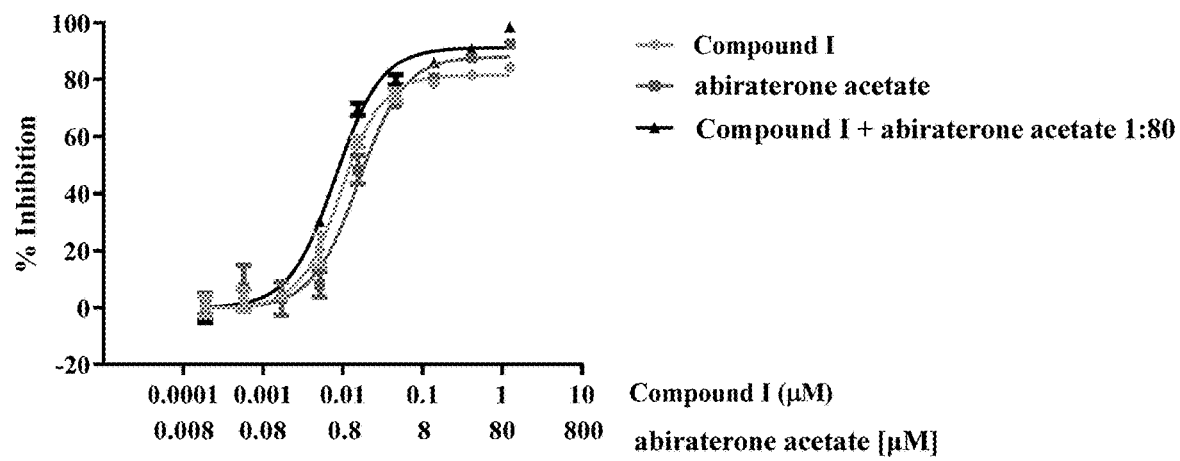
Figure 4D:
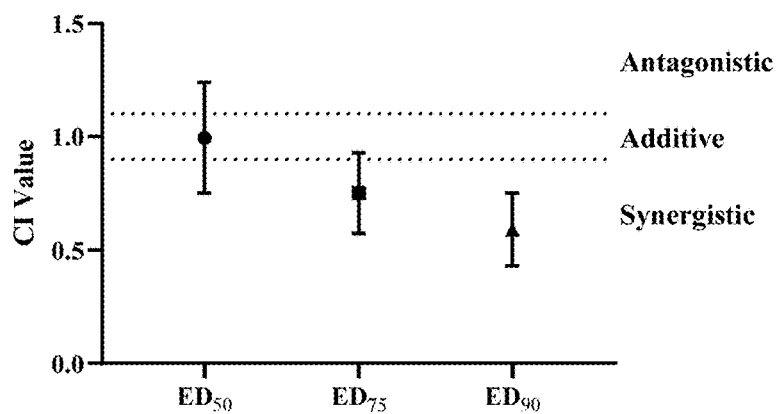
Figure 5C:
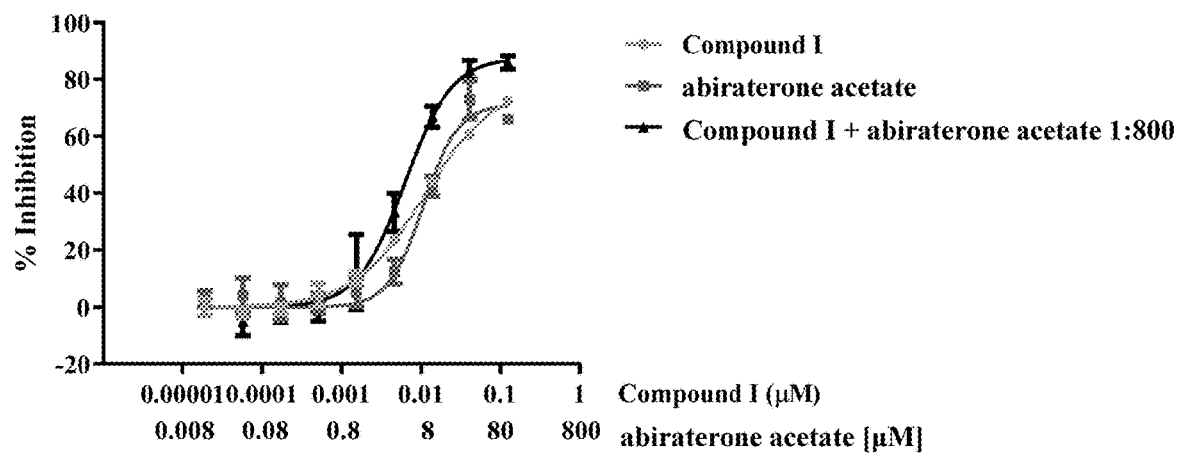
Figure 5D:
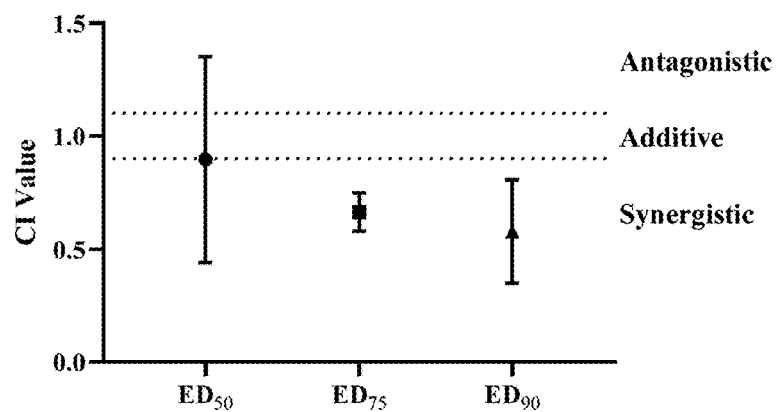

Combination of Compound I and abiraterone acetate at ratios of 1:80 in LNCaP cells and 1:800 in 22Rv1 cells were examined. The combination dose-responsive curve was slightly shifted in LNCaP cells and more prominently shifted in 22Rv1 cells to the left with respect to the two individual compound curves (FIG. 4C and FIG. 5C). CI values at $ED_{50}$, $ED_{75}$, and $ED_{95}$ are 1, 0.75 and 0.59, respectively, for LNCaP cells and 0.9, 0.66 and 0.58, respectively, for 22Rv1 cells indicating the synergistic interaction between Compound I and abiraterone acetate at $ED_{75}$, and $ED_{95}$ in LNCaP cells and 22Rv1 cells (FIG. 4D and FIG. 5D).

In summary, Compound I exerted potent anti-cancer activity against AR-positive prostate cancer cells, including those resistant to enzalutamide and abiraterone acetate. Compound I acted synergistically with enzalutamide or abiraterone acetate in either enzalutamide and abiraterone acetate sensitive or resistant cells. These data provide the rationale for clinical application of synergistic combinations of Compound I with anti-androgen agents, such as enzalutamide or abiraterone acetate, in treating castration-resistant prostate cancer.

Surprisingly, synergy between Compound I and abiraterone acetate is prone to be stronger at higher ED level than lower ED level in both cell lines compared to the synergy between Compound I and enzalutamide. Thus, synergy of Compound I and abiraterone acetate occurs at higher ED level that may provide a beneficial therapeutic effect.

TABLE 1

$IC_{50}$ Values for Compound I, Enzalutamide, and Abiraterone acetate in Prostate Cancer Cell Growth Assays

| Cell Line | Compound I | | | enzalutamide | | | Abiraterone acetate | | |
|---|---|---|---|---|---|---|---|---|---|
| | $IC_{50}$[a] (μM) | $CI_{95}$[b] (μM) | Repeat (n) | $IC_{50}$[a] (μM) | $CI_{95}$[b] (μM) | Repeat (n) | $IC_{50}$[a] (μM) | $CI_{95}$[b] (μM) | Repeat (n) |
| LNCaP | 0.043 | 0.024-0.077 | 3 | 6.8 | 4.7-9.9 | 3 | 3.5 | 2.3-5.5 | 3 |
| 22Rv1 | 0.034 | 0.019-0.061 | 3 | 51 | 45-58 | 3 | 42 | 28-64 | 3 |

[a]Geometric mean of the IC50
[b]95% Confidence Interval for geometric mean

Example 2

Figure 6A:
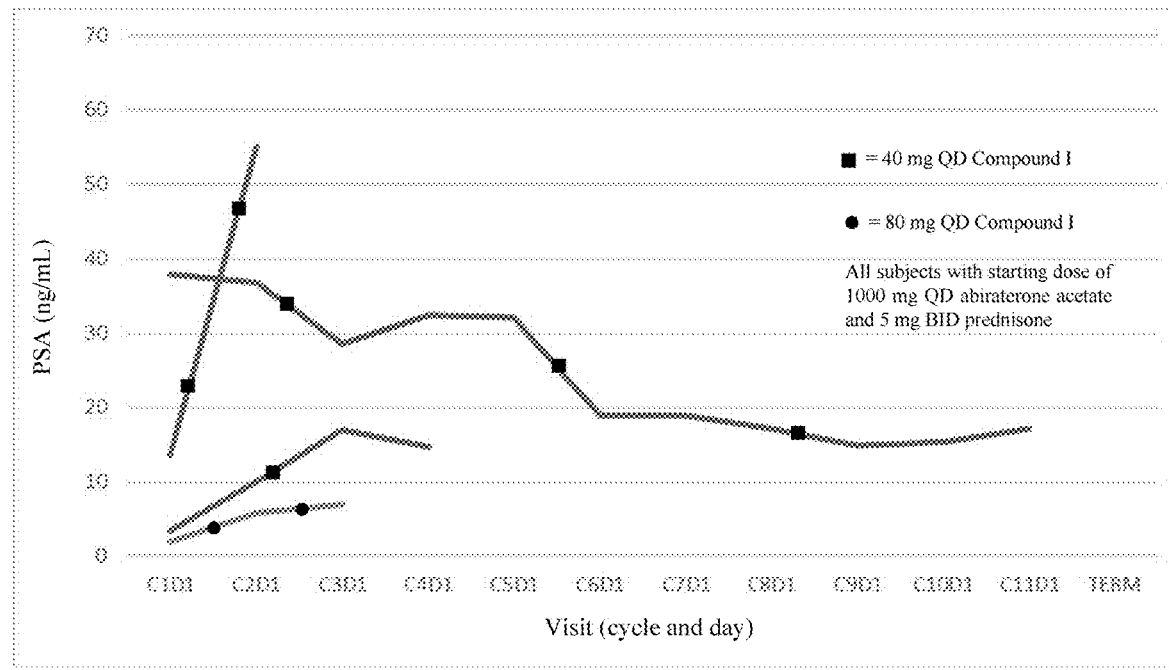
FIGS. 6A and 6B illustrate a combination of Compound I, and abiraterone acetate and prednisone in the treatment human patients.
Figure 6B:
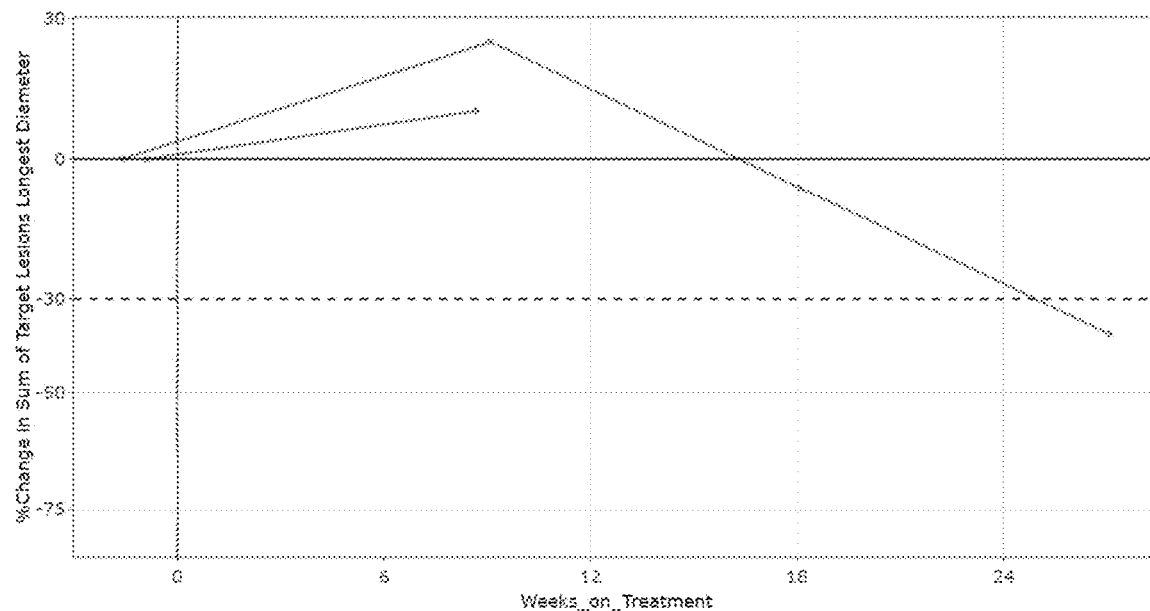

Combination Studies of (A) Compound I, (B) Abiraterone Acetate, and (C) Prednisone Two human patients were treated with 40 mg QD of Compound I in combination with 1000 mg QD of abiraterone acetate and 5 mg BID prednisone. One partial response was achieved after 9 cycles (each cycle is of 21 days) with 37.5% reduction in target lesions (FIG. 6A). One stable disease was achieved after 3 cycles with 10.3% increase in target lesions (FIG. 6A). FIG. 6B illustrates the spider plot % change in target lesions for the two subjects.

The third human patient was treated with 80 mg QD of Compound I in combination with 1000 mg QD of abiraterone acetate and 5 mg BID prednisone, but did not have a baseline response assessment (FIG. 6A).

Example 3

Combination Studies of (A) Compound I and (B) Olaparib

Figure 7A:
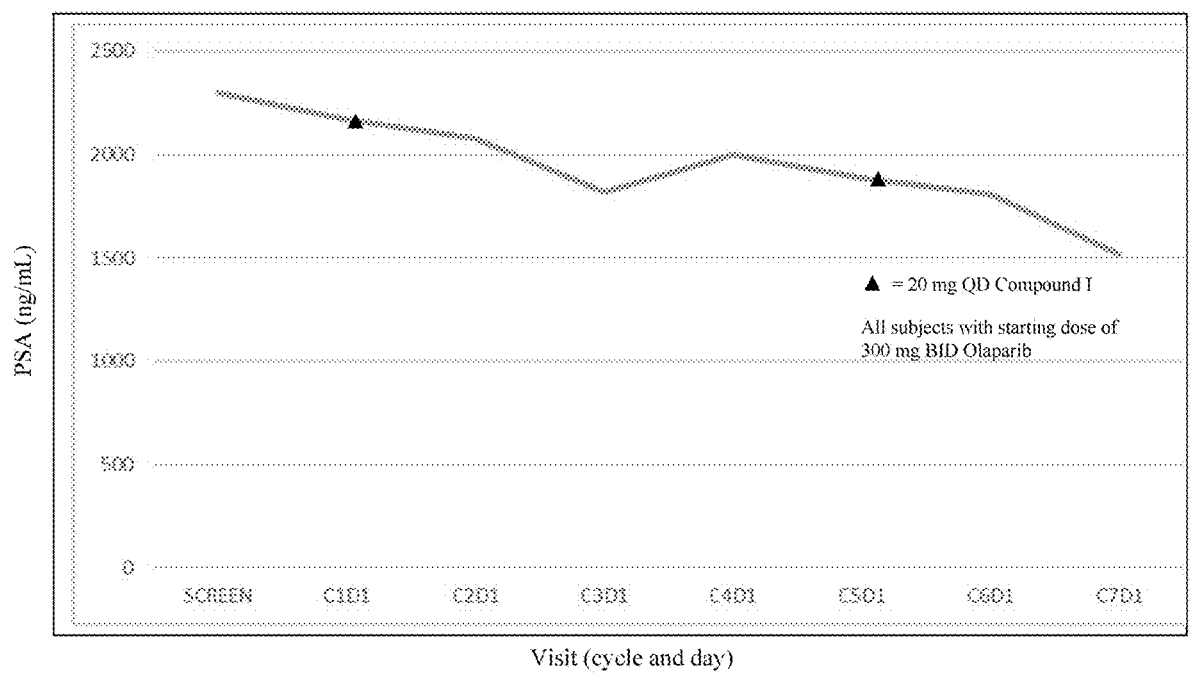
FIGS. 7A and 7B illustrate a combination of Compound I, and olaparib in the treatment of human patients.
Figure 7B:
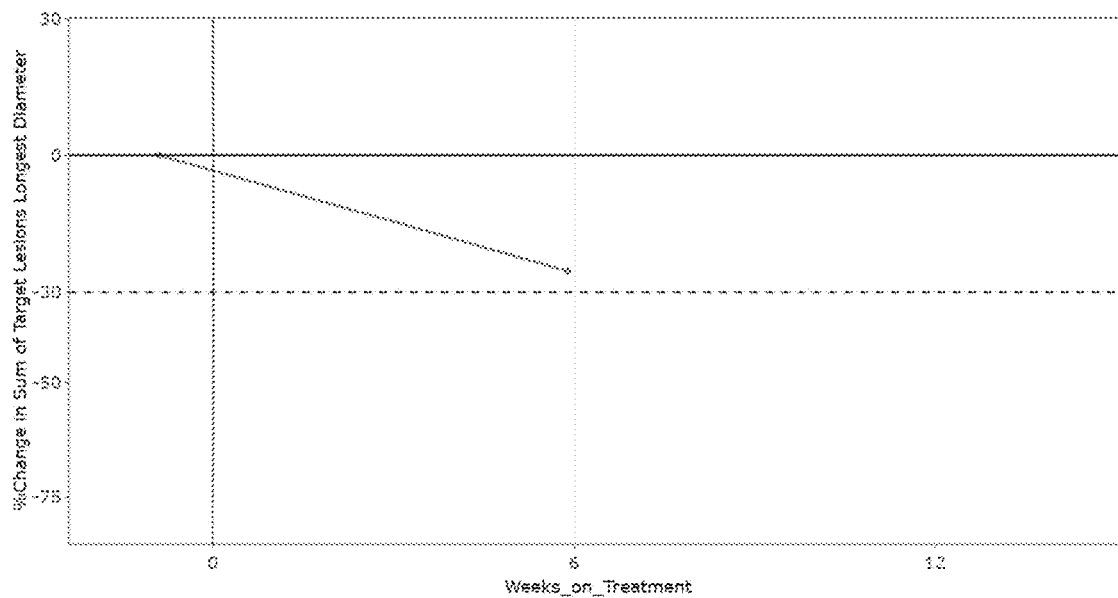

Three human patients were treated with 20 mg QD of Compound I in combination with 300 mg BID olaparib and one had post baseline response assessment. Stable disease was achieved after 2 cycles (each cycle is of 21 days) and was confirmed after 6 cycles with 25.4% reduction in target lesions (FIG. 7A). FIG. 7B illustrates the spider plot % change in target lesions for the patient.

REFERENCES

Cai L, Tsai Y H, Wang P, Wang J, Li D, Fan H, et al. ZFX mediates non-canonical oncogenic functions of the androgen receptor splice variant 7 in castrate-resistant prostate cancer. Mol Cell. 2018; 72(2):341-354.e6.

Chou T C. Theoretical basis, experimental design, and computerized simulation of synergism and antagonism in drug combination studies. Pharmacol Rev. 2006; 58(3): 621-681.

Chou T C. Drug Combination Studies and Their Synergy Quantification Using the Chou-Talalay Method. Cancer Res. 2010; 70(2).

Di Veroli G Y, Fornari C, Wang D, Mollard S, Bramhall J L, Richards F M, et al. Combenefit: an interactive platform for the analysis and visualization of drug combinations. Bioinformatics. 2016; 32(18):2866-2868.

Hara T, Miyazaki J, Araki H, Yamaoka M, Kanzaki N, Kusaka M, et al. Novel mutations of androgen receptor: a possible mechanism of bicalutamide withdrawal syndrome. Cancer Res. 2003; 63(1):149-153.

Hu X, Garcia C, Fazli L, Gleave M, Vitek M P, Jansen M, Inhibition of pten deficient castration resistant prostate cancer by targeting of the SET-PP2A signaling axis. Sci Rep. 2015; 5:15182.

Li Y, Chan S C, Brand L J, Hwang T H, Silverstein K A, Dehm S M. Androgen receptor splice variants mediate enzalutamide resistance in castration-resistant prostate cancer cell lines. Cancer Res. 2013; 73(2):483-489.

Liu C, Armstrong C, Zhu Y, Lou W, Gao A C. Niclosamide enhances abiraterone treatment via inhibition of androgen receptor variants in castration resistant prostate cancer. Oncotarget. 2016; 7(22):32210-32220.

Loewe S. The problem of synergism and antagonism of combined drugs. Arzneimittelforschung. 1953; 3(6):285-290.

Qi W, Morales C, Cooke L S, Johnson B, Somer B, Mahadevan D. Reciprocal feedback inhibition of the androgen receptor and PI3K as a novel therapy for castrate-sensitive and -resistant prostate cancer. Oncotarget. 2015; 6(39): 41976-41987.

All patents and other references cited herein are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of the embodiments described herein are exemplary and are not intended as limitations on the scope of the disclosure. Changes therein and other uses will occur to those skilled in the art, which are encompassed within the spirit of the disclosure, are defined by the scope of the claims.

It will be readily apparent to one skilled in the art that varying substitutions and modifications may be made to the present disclosure described herein without departing from the scope and spirit of the disclosure. For example, variations can be made to provide additional compounds of the compounds of this disclosure and/or various methods of administration can be used. Thus, such additional embodiments are within the scope of the present disclosure and the following claims.

The present disclosure illustratively described herein suitably may be practiced in the absence of any element or elements, limitation or limitations which is not specifically described herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically described by the embodiments and optional features, modification and variation of the concepts herein described may be resorted to by those skilled in the art, and that such modifications and variations are considered to be within the scope of this disclosure as defined by the appended claims.

In addition, where features or aspects of the disclosure are described in terms grouping of alternatives, those skilled in the art will recognize that the disclosure is also thereby described in terms of any individual member or subgroup of members of the groups described herein.

Also, unless indicated to the contrary, where various numerical values are provided for embodiments, additional embodiments are described by taking any 2 different values as the endpoints of a range. Such ranges are also within the scope of the present disclosure.

Thus, additional embodiments are within the scope of the disclosure and within the following claims.

The invention claimed is:

1. A method of treating a subject suffering from a cancer, comprising administering to the subject a synergistic combination of agents comprising:
(a) Compound I:

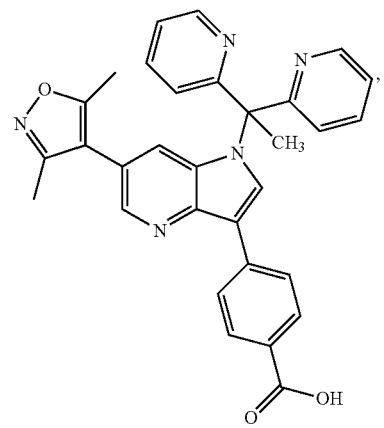

or a pharmaceutically acceptable salt thereof; and
(b) one or more inhibitors of the androgen receptor signaling pathway; or
(c) one or more PARP inhibitors;
wherein the combination of agents is administered in an amount that is therapeutically effective in the treatment;
wherein the cancer is metastatic castration resistant prostate cancer, and wherein the treatment is initiated after the subject with metastatic castration resistant prostate cancer develops disease progression while currently receiving treatment with abiraterone acetate and prednisone or prednisolone.

2. The method according to claim 1, wherein the subject is a human.

3. The method according to claim 1, wherein Compound I, or a pharmaceutically acceptable salt thereof, is administered in the form of a tablet that comprises Compound I.

4. The method according to claim 1, wherein the subject is administered Compound I with one or more inhibitors of the androgen receptor signaling pathway comprising one or more cytochrome P450-17A1 inhibitors independently selected from the group consisting of abiraterone, abiraterone acetate, ketoconazole, seviteronel, orteronel, galeterone, and CFG920, or a pharmaceutically acceptable salt thereof.

5. The method according to claim 4 wherein the cytochrome P450-17A1 inhibitor is abiraterone or abiraterone acetate.

6. The method according to claim 4 wherein the cytochrome P450-17A1 inhibitor is abiraterone acetate.

7. The method according to claim 4 further comprising administering a corticosteroid, wherein the amount of the combination of agents is therapeutically effective in the treatment.

8. The method according to claim 7, wherein the corticosteroid is prednisone or prednisolone.

9. The method according to claim 1, wherein the one or more PARP inhibitors are independently selected from the group consisting of olaparib, niraparib, rucaparib, talazoparib, and veliparib, or a pharmaceutically acceptable salt thereof.

10. The method according to claim 9, wherein the PARP inhibitor is olaparib or a pharmaceutically acceptable salt thereof.

11. The method according to claim 1, wherein Compound I, or a pharmaceutically acceptable salt thereof, is administered in an amount of from about 5 mg/day to about 200 mg/day.

12. The method according to claim 11, wherein Compound I, or a pharmaceutically acceptable salt thereof, is administered in an amount of from about 10 mg/day to about 100 mg/day.

13. The method according to claim 12, wherein Compound I, or a pharmaceutically acceptable salt thereof, is administered in an amount of from about 20 mg/day to about 80 mg/day.

14. The method according to claim 8, wherein Compound I, or a pharmaceutically acceptable salt thereof, is administered in an amount of from about 5 mg/day to about 200 mg/day; abiraterone acetate is administered in an amount of from about 500 mg/day to about 1500 mg/day; and prednisone or prednisolone is administered in an amount of from about 2 mg/day to about 40 mg/day.

15. The method according to claim 14, wherein Compound I, or a pharmaceutically acceptable salt thereof, is administered in an amount of from about 10 mg/day to about 100 mg/day; abiraterone acetate is administered in an amount of from about 750 mg/day to about 1250 mg/day; and prednisone or prednisolone is administered in an amount of from about 5 mg/day to about 20 mg/day.

16. The method according to claim 15, wherein Compound I, or a pharmaceutically acceptable salt thereof, is administered in an amount of from about 20 mg/day to about 80 mg/day; abiraterone acetate is administered in an amount of about 1000 mg/day; and prednisone or prednisolone is administered in an amount of about 10 mg/day.

17. The method according to claim 16, wherein Compound I, or a pharmaceutically acceptable salt thereof, is administered in an amount of from about 20 mg/day to about 80 mg/day; 1000 mg abiraterone acetate are administered orally once daily; and 5 mg prednisone or prednisolone are administered orally twice daily.

18. The method according to claim 17, wherein prednisone or prednisolone is taken at least 2 hours before Compound I and abiraterone acetate or 1 hour after taking Compound I and abiraterone acetate.

19. The method according to claim 5, wherein Compound I and abiraterone acetate are administered to the subject at the same time.

20. The method according to claim 10, wherein Compound I, or a pharmaceutically acceptable salt thereof, is administered in an amount of from about 5 mg/day to about 200 mg/day; and olaparib, or a pharmaceutically acceptable salt thereof, is administered in an amount of from about 300 mg/day to about 900 mg/day.

21. The method according to claim 20, wherein Compound I, or a pharmaceutically acceptable salt thereof, is administered in an amount of from about 10 mg/day to about 100 mg/day; and olaparib, or a pharmaceutically acceptable salt thereof, is administered in an amount of from about 500 mg/day to about 700 mg/day.

22. The method according to claim 21, wherein Compound I, or a pharmaceutically acceptable salt thereof, is administered in an amount of from about 20 mg/day to about 80 mg/day; and olaparib, or a pharmaceutically acceptable salt thereof, is administered in an amount of about 600 mg/day.

23. The method according to claim 22, wherein 300 mg tablet of olaparib is administered orally administered to the subject twice daily.

24. The method according to claim 23, wherein a morning dose of olaparib is administered to the subject at the same time as Compound I.

25. The method according to claim 20, wherein the subject has deleterious or suspected deleterious germline or somatic homologous recombination repair (HRR) gene-mutated metastatic castration-resistant prostate cancer.

* * * * *